US009085803B2

(12) United States Patent
Hosomi

(10) Patent No.: US 9,085,803 B2
(45) Date of Patent: Jul. 21, 2015

(54) PROBE FOR DETECTION OF POLYMORPHISM IN ABL GENE, AND USE THEREOF

(75) Inventor: Toshiya Hosomi, Kyoto (JP)

(73) Assignee: ARKRAY, Inc., Seoul (KR)

( * ) Notice: Subject to any disclaimer, the term of this patent is extended or adjusted under 35 U.S.C. 154(b) by 324 days.

(21) Appl. No.: 13/180,306

(22) Filed: Jul. 11, 2011

(65) Prior Publication Data

US 2012/0009576 A1    Jan. 12, 2012

(30) Foreign Application Priority Data

Jul. 12, 2010    (JP) ................................. 2010-158254

(51) Int. Cl.
| C07H 21/02 | (2006.01) |
| C07H 21/04 | (2006.01) |
| C12Q 1/68 | (2006.01) |
| C12P 19/34 | (2006.01) |

(52) U.S. Cl.
CPC ........ *C12Q 1/6886* (2013.01); *C12Q 2600/106* (2013.01); *C12Q 2600/156* (2013.01)

(58) Field of Classification Search
CPC ........... C12Q 1/6886; C12Q 2600/106; C12Q 2600/156; C12Q 1/485; C12Q 2600/136; C12Q 2561/125; C12Q 1/6827; C12Q 2537/143; C12Q 1/6837; C12Q 1/686; C12Q 1/6858; C12Q 1/6816; C12Q 2535/131; C12Q 2525/161; C12Q 2531/113
See application file for complete search history.

(56) References Cited

U.S. PATENT DOCUMENTS

| 5,780,229 A * | 7/1998 | Newman ..................... 435/6.12 |
| 6,699,661 B1 | 3/2004 | Kurane et al. .................... 435/6 |
| 7,354,707 B2 | 4/2008 | Kurane et al. .................... 435/6 |
| 2009/0176231 A1* | 7/2009 | Hirai et al. ........................ 435/6 |
| 2009/0197893 A1* | 8/2009 | Lee et al. .................. 514/252.19 |
| 2010/0216123 A1 | 8/2010 | Hirai et al. ........................ 435/6 |

FOREIGN PATENT DOCUMENTS

| EP | 2 025 764 | 2/2009 | ............... C12Q 1/68 |
| EP | 2 031 074 | 3/2009 | ............... C12Q 1/68 |
| JP | 2001-286300 | 10/2001 | |
| JP | 2002-119291 | 4/2002 | |
| JP | 2004-537992 | 12/2004 | |
| JP | 2008-199965 | 9/2008 | |
| WO | WO 02/14555 | 2/2002 | ............... C12Q 1/68 |
| WO | WO 02/102976 | 12/2002 | |
| WO | WO 2007/109527 | 9/2007 | ............ G01N 33/50 |
| WO | WO 2008/018305 | 2/2008 | |
| WO | WO 2008/033776 | 3/2008 | ............... C12Q 1/68 |

OTHER PUBLICATIONS

Polakova (Leukemia Research vol. 32 pp. 1236-1243 2008).*
GenBank (Accession No. NM_005157.3 GI:62362413 (Apr. 7, 2005)).*
Office Action issued in corresponding Korean Patent Application No. 10-2011-0068755 dated May 29, 2013.
Ernst et al., "ABL single nucleotide polymorphisms may masquerade as BCR-ABL mutations associated with resistance to tyrosine kinase inhibitors in patients with chronic myeloid leukemia," Haematologica, 93: 1389-1393 (2008).
Partial European Search Report in corresponding European Application No. 11173645.0 (mailed Oct. 20, 2011).
Crockett et al., "Fluorescein-Labeled Oligonucleotides for Real-Time PCR: Using the Inherent Quenching of Deoxyguanosine Nucleotides", Analytical Biochemistry, 290(1):89-97 (2001).
Lyon et al., "LightCycler Technology in Molecular Diagnostics," Journal of Molecular Diagnostics, 11: 93-101 (2009).
Soverini et al., "Contribution of ABL Kinase Domain Mutations to Imatinib Resistance in Different Subsets of Philadelphia-Positive Patients: by the GIMEMA Working Party on Chronic Myeloid Leukemia", Clin Cancer Res, 23(24): 7374-7379 (Dec. 15, 2006).
Notice of Allowance issued in corresponding Korean Patent Application No. 10-2011-0068755 dated Jan. 7, 2014.
Furukawa et al., "Reduction-triggered red fluorescent probes for dual-color detection of oligonucleotide sequences", Organic & Biomolecular Chemistry, 7: 671-677 (2009).
Hochhaus *et al.*, "Molecular and chromosomal mechanisms of resistance to imatinib (STI571) therapy", Leukemia, 16:2190-2196 (2002).
Roumiantsev *et al.*, "Clinical resistance to the kinase inhibitor STI-571 in chronic myeloid leukemia by mutation of Tyr-253 in the Abl Kinase domain P-loop", PNAS, 99(16):10700-10705 (Aug. 6, 2002).
Soverini *et al.*, "Contribution of ABL Kinase Domain Mutations to Imatinib Resistance in Different Subsets of Philadelphia-Positive Patients: by the GIMEMA Working Party on Chronic Myeloid Leukemia", Clin Cancer Res, 12(24):7374-7379 (Dec. 15, 2006).

* cited by examiner

*Primary Examiner* — Amanda Haney

(74) *Attorney, Agent, or Firm* — Morgan, Lewis & Bockius LLP

(57) ABSTRACT

A probe for detecting a polymorphism in abl gene, comprising at least one fluorescence-labeled oligonucleotide.

10 Claims, 9 Drawing Sheets

(A)

(B)

(I)

(II)

(III)

WAVE3 : diff curve

WAVE3 : diff curve

PROBE FOR DETECTION OF POLYMORPHISM IN ABL GENE, AND USE THEREOF

CROSS-REFERENCE TO RELATED APPLICATION

This application claims priority under 35 USC 119 from Japanese Patent Application No. 2010-158254, filed on Jul. 12, 2010, which is incorporated by reference in its entirety.

SEQUENCE LISTING SUBMISSION VIA EFS-WEB

A computer readable text file, entitled "068022-5121-SequenceListing.txt," created on or about Jul. 11, 2011 with a file size of about 8 kb contains the sequence listing for this application and is hereby incorporated by reference in its entirety.

TECHNICAL FIELD

The present invention relates to a probe for detecting a polymorphism in the abl gene, which is involved in leukemia, and use thereof.

BACKGROUND ART

Leukemia is a disease caused by canceration of hematopoietic stem cells in bone marrow. In particular, chronic myeloid leukemia (CML) is known to be caused by the bcr-abl fusion gene formed by translocation between chromosome 9 and chromosome 22, and an ABL kinase inhibitor imatinib or the like is widely used for its therapy. However, there is a problem in that, in cases where a point mutation exists in this abl gene (including the abl gene in the fusion gene), resistance to imatinib is expressed. In such cases, the dose of imatinib needs to be increased; the therapeutic agent needs to be changed; or the therapy needs to be switched to bone marrow transplantation. Therefore, in therapy of leukemia, especially CML, it is very important to detect the presence/absence of a point mutation in the abl gene.

Examples of the method for detecting a point mutation in the abl gene include a method wherein an abl gene mutation is amplified by RT-PCR and cloned, followed by sequencing analysis thereof (PNAS Aug. 6, 2002 vol. 99 no. 16 10700-10705); a method wherein an abl gene mutation is detected by the PCR-RFLP method (Leukemia (2002) 16, 2190-2196), and a method wherein an abl gene mutation is detected by the DHPLC method and subjected to sequencing analysis (Clin Cancer Res 2006; 12(24) Dec. 15, 2006). However, the method described in PNAS 2002 requires expertise and skill for the experimental operation, and automation is difficult. Further, the experimental operation is laborious, and it takes several days to obtain a result. The method described in Leukemia 2002 also requires laborious operation, and it takes about 1 day to obtain a result. Further, the amplification product may cause contamination in another reaction. Further, its automation is difficult. The method described in Clin Cancer Res 2006 also requires laborious operation, and its automation is difficult. Further, in the DHPLC method, discrimination of mutant types is difficult, so that the mutant type needs to be separately detected by sequencing or the like.

Because of these problems, in recent years, as a method of detecting a polymorphism, detection using melting curve analysis (Tm analysis) has been carried out (JP 2001-286300 A, JP 2002-119291 A). In this method, a probe complementary to the sequence to be detected which contains a genetic polymorphism to be detected is used and a target single-stranded DNA in the detection sample is allowed to form a hybrid (double-stranded DNA) with the probe. This hybrid-forming body is subjected to heat treatment, and dissociation (melting) of the hybrid due to increased temperature is detected by measurement of a signal such as the absorbance. Based on the detection result, the Tm value is determined, thereby judging the presence/absence of the polymorphism of interest. The Tm value increases as the homology in the hybrid-forming body increases, while the value decreases as the homology decreases. Therefore, the Tm value (evaluation criterion value) of the hybrid-forming, body between the sequence to be detected containing the polymorphism and of interest and the probe complementary thereto is preliminarily determined, and the Tm value (measure value) between the target single-stranded DNA in the detection sample and the probe is measured, and, in cases where the measured value is the same as the evaluation criterion value, the result can be judged as "matching", which means that the target DNA has the polymorphism of interest, while in cases where the measured value is lower than the evaluation criterion value, the result can be judged as "mismatching", which means that the target DNA does not have the polymorphism of interest.

However, there is a problem in that such a detection method using Tm analysis has a low sensitivity. This is especially problematic when a point mutation is to be detected from DNA derived from blood cells of a leukemia patient (Japanese Translated PCT Patent Application Laid-open No. 2004-537992). That is, even in blood of a single CML patient, blood cells having a point mutation generated in the abl gene (mutant gene) and blood cells having no such mutation (normal gene) are contained, and the only difference between them is a point mutation, that is, the sequence of a single nucleotide. This leads to a phenomenon wherein the probe for detection of a point mutation hybridizes (matches) with a mutant sequence having the point mutation (sequence to be detected), while hybridizing (mismatches) also with the normal sequence which does not have the point mutation (sequence not to be detected). In such cases, there is a problem in that, when the melting curve indicating the relationship between the signal strength and the temperature is prepared by the Tm analysis, detection of the peak in the higher-temperature side, which is the peak for the matched mutant sequence, is difficult because of the existence of the peak in the lower-temperature side, which is the peak for the mismatched normal sequence. That is, in conventional probes, there is a problem in that, even in cases where a mutant sequence containing a mutation exists, its detection is difficult because of the existence of the normal sequence which does not contain the mutation, so that the detection sensitivity decreases.

In WO2008/018305, probes to be employed in a detection method using Tm analysis are described, and those probes are used to detect A758T(Y253F), G756C(Q250E), G763A (E255K) and A758T(Y253F), which are point mutations in the abl gene. Further, in JP 2008-199965 A, probes for detecting A730G(M244V), G749A(G250E), A943 G(T315A), C944T(T315I), C951G(F317L), T1052C(M351T), A1064G (E355G), T1075G(F359V) and A1187G(H396R) are described. However, probes for detecting T10760 (F359C), T757C (Y253H), A764T (E255V) and G895C/T (V299L) have not been described in any literature.

SUMMARY OF THE INVENTION

The present invention aims to specify probes effective for detecting T1076G (F359C), T757C (Y253H), A764T (E255V) and G895C/T (V299L), which are point mutations in the ab1 gene, and to provide a method for detecting T1076G (F359C), T757C (Y253H), A764T (E255V) and G895C/T (V299L), which are point mutations in the ab1 gene, and a reagent kit therefor.

The present inventors discovered that, by designing probes based on particular regions containing T1076G (F359C), T757C (Y253H), A764T (E255V) and G895C/T (V299L), which are point mutations in the ab1 gene, and carrying out Tm analysis using the probes, polymorphisms in the mutation sites can be detected, thereby completing the present invention.

That is, the present invention includes the following inventions.

(1) A probe for detecting a polymorphism in ab1 gene, said probe comprising at least one fluorescene-labeled oligonucleotide P1 to P9 below:

(P1) an obligonucleotide comprising a nucleotide sequence complementary to a nucleotide sequence of 10 to 50 consecutive nucleotides containing nucleotides 125 to 133 in SEQ ID NO:1 or 2 or a homologous sequence thereof, wherein the nucleotide corresponding to the nucleotide at position 125 is cytosine and labeled with a fluorescent dye;

(P2) an oligonucleotide comprising a nucleotide sequence complementary to a nucleotide sequence of 12 to 50 consecutive nucleotides containing nucleotides 135 to 146 in SEQ ID NO:3 or 4 or a homologous sequence thereof, wherein the nucleotide corresponding to the nucleotide at position 146 is cytosine and labeled with a fluorescent dye;

(P3) an oligonucleotide comprising a nucleotide sequence complementary to a nucleotide sequence of 10 to 50 consecutive nucleotides containing nucleotides 135 to 144 in SEQ ID NO:3 or 4 or a homologous sequence thereof, wherein the nucleotide corresponding to the nucleotide at position 144 is cytosine and labeled with a fluorescent dye;

(P3') an oligonucleotide comprising a nucleotide sequence complementary to a nucleotide sequence of 10 to 50 consecutive nucleotides containing nucleotides 142 to 144 in SEQ ID NO:3 or 5 or a homologous sequence thereof, wherein the nucleotide corresponding to the nucleotide at position 144 is cytosine and labeled with a fluorescent dye;

(P4) an oligonucleotide comprising a nucleotide sequence complementary to a nucleotide sequence of 10 to 50 consecutive nucleotides containing nucleotides 134 to 135 in SEQ ID NO:3 or 4 or a homologous sequence thereof wherein the nucleotide corresponding to the nucleotide at position 134 is cytosine and labeled with a fluorescent dye;

(P5) an oligonucleotide comprising a nucleotide sequence complementary a nucleotide sequence of 10 to 0.50 consecutive nucleotides containing nucleotides 138 to 142 in SEQ ID NO:3 or 5 or a homologous sequence thereof, wherein the nucleotide corresponding to the nucleotide at position cytosine and labeled with a fluorescent dye;

(P6) an oligonucleotide comprising a nucleotide sequence complementary to a nucleotide sequence of 12 to 50 consecutive nucleotides containing nucleotides 142 to 153 in SEQ ID NO:3 or 5 or a homologous sequence thereof, wherein the nucleotide corresponding to the nucleotide at position 153 is cytosine and labeled with a fluorescent dye;

(P7) an oligonucleotide comprising a nucleotide sequence complementary to a nucleotide sequence of 10 to 50 consecutive nucleotides containing nucleotides 142 to 150 in SEQ ID NO:3 or 5 or a homologous sequence thereof wherein the nucleotide corresponding to the nucleotide at position 150 is cytosine and labeled with a fluorescent dye;

(P8) an oligonucleotide comprising a nucleotide sequence of 10 to 50 consecutive nucleotides containing nucleotides 126 to 135 in one of SEQ ID NOs:6 to 8 or a homologous sequence thereof, wherein the nucleotide corresponding to the nucleotide at position 135 is cytosine and labeled with a fluorescent dye; and (P9) an oligonucleotide comprising a nucleotide sequence of 10 to 50 consecutive nucleotides containing nucleotides 126 to 129 in one of SEQ ID NOs:6 to 8 or a homologous sequence thereof, wherein the nucleotide corresponding to the nucleotide at position 129 is cytosine and labeled with a fluorescent dye.

(2) The probe according to (1), wherein
said oligonucleotide P1 has the nucleotide corresponding to the nucleotide at position 125 labeled with a fluorescent dye at the first, second or third position from the 3'-end;
said oligonucleotide P2 has the nucleotide corresponding to the nucleotide at position 146 labeled with a fluoresce dye at the first, second or third position from the 5'-end;
said oligonucleotide P3 and P3' have the nucleotide corresponding to the nucleotide at position 144 labeled with a fluorescent dye at the first, second or third position from the 5'-end;
said oligonucleotide P4 has the nucleotide corresponding to the nucleotide at position 134 labeled with a fluorescent dye at the first, second or third position from the 3'-end;
said oligonucleotide P5 has the nucleotide corresponding to the nucleotide at position 138 labeled with a fluorescent dye at the first, second or third position from the 3'-end;
said oligonucleotide P6 has the nucleotide corresponding to the nucleotide at position 153 labeled with a fluorescent dye at the first, second or third position from the 5'-end;
said oligonucleotide P7 has the nucleotide corresponding to the nucleotide at position 150 labeled with a fluorescent dye at the first, second or third position from the 5'-end;
said oligonucleotide P8 has the nucleotide corresponding to the nucleotide at position 135 labeled with a fluorescent dye at the first, second or third position from the 3'-end; and
said oligonucleotide P9 has the nucleotide corresponding to the nucleotide at position 129 labeled with a fluorescent dye at the first, second or third position from the 3'-end.

(3) The probe according to (1), wherein
said oligonucleotide P1 has the nucleotide corresponding to the nucleotide at position 125 labeled with a fluorescent dye at the 3'-end;
said oligonucleotide P2 has the nucleotide corresponding to the nucleotide at position 146 labeled with a fluorescent dye at the 5'-end;
said oligonucleotide P3 and P3' have the nucleotide corresponding the nucleotide at position 144 labeled with a fluorescent dye at the 5'-end;
said oligonucleotide P4 has the nucleotide corresponding to the nucleotide at position 134 labeled with a fluorescent dye at the 3'-end;
said oligonucleotide P5 has the nucleotide corresponding to the nucleotide at position 138 labeled with a fluorescent dye at the 3'-end;
said oligonucleotide P6 has the nucleotide corresponding to the nucleotide at position 153 labeled with a fluorescent dye at the 5'-end;
said oligonucleotide P7 has the nucleotide corresponding to the nucleotide at position 150 labeled with a fluorescent dye at the 5'-end; said oligonucleotide P8 has the nucleotide corresponding to the nucleotide at position 135 labeled with a fluorescent dye at the 3'-end; and said oligonucleotide P9 has the nucleotide corresponding to the nucleotide at position 129 labeled with a fluorescent dye at the 3'-end.

(4) The probe according to (1), wherein said oligonucleotide emits fluorescence when the oligonucleotide is not hybridized with a target sequence, and the fluorescence intensity decreases or increases when the oligonucleotide is hybridized with the target sequence.

(5) The probe according to (4), wherein said oligonucleotide emits fluorescence when the oligonucleotide is not hybridized with a target sequence, and the fluorescence intensity decreases when the oligonucleotide is hybridized with the target sequence.

(6) The probe according to (1), wherein said oligonucleotides P1, P3, P3', P4, P5, P7, P8 and P9 have 10 to 30 consecutive nucleotides and said oligonucleotides P2 and P6 have 12 to 30 consecutive nucleotides.

(7) The probe according to (1), wherein said probe is a probe for melting curve analysis.

(8) A method for detecting a polymorphism in ab1 gene, which method comprises using the probe according to (1).

(9) A method for detecting a polymorphism in ab1 gene, said method comprising:

(I) bringing the probe according to (1) into contact with a sample containing DNA to allow said probe to hybridize with said DNA;

(II) changing the temperature to dissociate the hybrid-forming body between said DNA and said probe, and measuring fluctuation of a signal due to the dissociation of the hybrid-forming body;

(III) determining Tm value by analyzing said fluctuation of a signal; and (IV) determining the presence/absence of the polymorphism of interest or abundance ratio of a nucleotide sequence (s) having the polymorphism, based on said Tm value.

(10) The method according to (9), further comprising amplifying the DNA before said Step (I) or at the same time with said Step (I).

(11) A method for judging resistance to an antileukemic agent or judging a pharmacological effect of an antileukemic agent, said method comprising detecting a polymorphism in ab1 gene by the method according to (8) and judging the resistance to the antileukemic agent or judging the pharmacological effect of the antileukemic agent based on the presence/absence of the polymorphism.

(12) A reagent kit for detecting a polymorphism in ab1 gene, said kit comprising the probe according to (1).

(13) The reagent kit according to (12), further comprising primer(s) for amplifying, in ab1 gene, a region in the nucleotide sequence shown in SEQ ID NO:1, said region comprising a sequence with which the oligonucleotide P1 hybridizes; a region in the nucleotide sequence shown in SEQ ID NO:3, said region comprising a sequence with which the oligonucleotide P2. P3, P3'. P4, P5. P6 or P7 hybridizes or a region in the nucleotide sequence shown in SEQ ID NO:6, said comprising a sequence with which the oligonucleotide P8 or P9 hybridizes.

It should be noted that the polymorphisms of the ab1 gene described above also include polymorphisms in the vicinity of the gene.

By the probe of the present invention, even in the coexistence of the ab1 gene having the mutation to be detected (also including the ab1 gene in the bcr-ab1 fusion gene; this provision is also applied hereinafter) (mutant gene) and the ab1 gene having no such mutation (normal gene), the sequence to be detected having the mutation of interest can be detected. In Tm analysis, in cases where the probe hybridizes with both a mutant gene different in only one nucleotide and the normal gene, the signals for the both genes overlap with each other in the melting curve, so that detection of existence of the mutant gene is very difficult. On the other hand, in cases where the probe of the present invention is employed, although it hybridizes with both the mutant gene and the normal gene, the both signals can be sufficiently separated from each other in the melting curve. Thus, by the present invention, a mutant gene can be detected with a higher sensitivity than before.

By including the probe of the present invention in a gene amplification system such as PCR and only carrying out Tm analysis after the gene amplification reaction, typing of plural gene variants is possible at a high sensitivity. Further, since whole blood, an oral mucosa suspension and the like can be directly tested, labor and cost can be reduced.

The probe of the present invention has a high specificity and a high detection sensitivity.

By using the method of the present invention, even in cases where PCR is carried out, the amplification product does not need to be extracted, so that there is hardly the risk of contamination. Further, since the method of the present can be carried out by a simple procedure, it can be easily automated.

DESCRIPTION OF THE PREFERRED EMBODIMENTS

Figure 1:
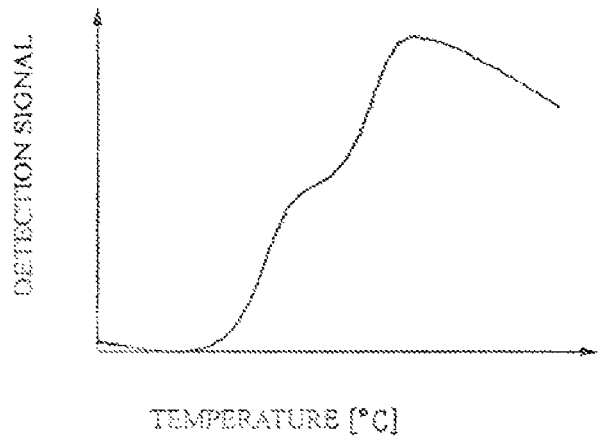
FIG. 1 shows diagrams showing examples of (A) a melting curve of a nucleic acid mixture and (B) a differential melting curve.
Figure 1:
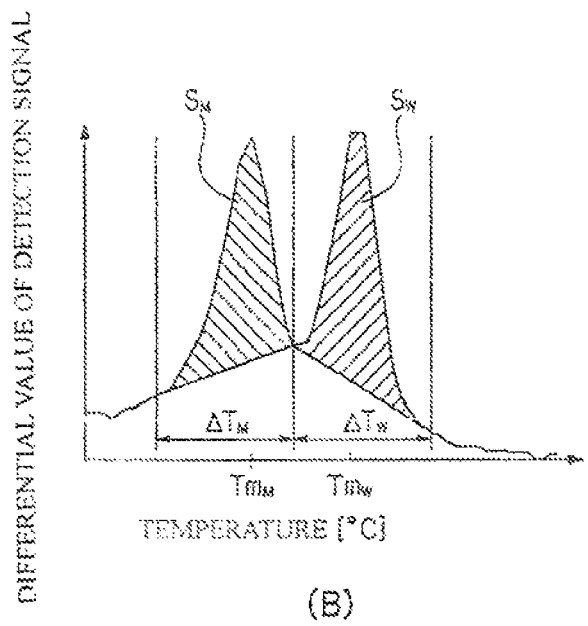

In the present invention, the abl gene having the mutation to be detected is also referred to as the "mutant gene"; the sequence having such mutation to be detected is referred to as the "mutant sequence"; the abl gene having no such mutation to be detected is also referred to as the "normal gene"; the sequence having no such mutation to be detected is also referred to as the "normal sequence"; and the DNA in the sample from which the presence/absence of a mutation is to be detected is also referred to as the "target DNA".

Examples of the polymorphism to be detected in the present invention include single nucleotide polymorphisms (SNPs).

In the present specification. TI 076G (F359C) represents the mutation from T (wild type) to G (variant) at nucleotide position 1076 of the abl gene, and the description the parentheses means that the mutation of the nucleotide causes change in the 359th amino acid from F to C. Other mutations are also represented in the same manner.

The nucleotide sequence of the abl gene is registered in National Center for Biotechnology Information (NCBI) under accession No. NG_012034. All of the sequences of SEQ ID NOs:1, 3 and 6 described below are also included these sequences.

The probe of the present invention is described below.
<Probe>

As mentioned above, the probe of the present invention is a probe for detecting a polymorphism in abl gene, and comprises at least one oligonucleotide selected from the group consisting of the P1 to P9.

(P1) An oligonucleotide comprising a nucleotide sequence complementary to a nucleotide sequence of 10 to 50 consecutive nucleotides containing nucleotides 125 to 133 in SEQ ID NO:1 or 2 or a homologous sequence thereof, wherein the nucleotide corresponding to the nucleotide at position 125 is cytosine and labeled with a fluorescent dye.

Here, the "nucleotide corresponding to the nucleotide at position 125" means, in the complementary or homologous sequence, the complementary nucleotide c (cytosine) which corresponds to g (guanine) at nucleotide position 125 in SEQ ID NOs:1 and 2. In the P1 probe, this c preferably exists at the first, second or third position from the 3'-end, more preferably exists at the 3'-end.

The probe composed of the oligonucleotide P1 is a probe for detecting a polymorphism at nucleotide position 133 in the nucleotide sequence of SEQ ID NO:1. This nucleotide corresponds to the nucleotide for the T1076G mutation, and the nucleotide is T in the of the wild type, and G in the case of the variant. Sequences of a region containing T1076 are shown. SEQ ID NOs:1 (the wild type having T at position 133) and 2 (the variant having G at position 133).

The probe for detection of the polymorphism has a length of preferably 10 to 30 consecutive nucleotides, more preferably 15 to 25 consecutive nucleotides.

The probe composed of the oligonucleotide P1 may comprise either one or both of an oligonucleotide for detection of the wild type, comprising a nucleotide sequence complementary to a nucleotide sequence of 10 to 50 consecutive nucleotides containing nucleotides 125 to 133 in SEQ ID NO:1 or a homologous sequence thereof, wherein the nucleotide corresponding to the nucleotide at position 125 is cytosine and labeled with a fluorescent dye; and an oligonucleotide for detection of the variant, comprising a nucleotide sequence complementary to a nucleotide sequence of 10 to 50 consecutive nucleotides containing nucleotides 125 to 133 in SEQ ID NO:2 or a homologous sequence thereof, wherein the nucleotide corresponding to the nucleotide at position 125 is cytosine and labeled with a fluorescent dye.

The probe preferably has the nucleotide sequence of SEQ ID NO:9 described below, which probe is for detection of the variant:

```
5'-cctgtggatgCagtttttc*-3'      (SEQ ID NO: 9)
``` wherein c* indicates c which is fluorescence-labeled at its 3'-side (this provision is also applied hereinafter).

In the corresponding probe for detection of the wild type, the uppercase C is replaced with A.

(P2) An oligonucleotide comprising a nucleotide sequence complementary a nucleotide sequence of 12 to 50 consecutive nucleotides containing nucleotides 135 to 146 in SEQ ID NO:3 or 4 or a homologous sequence thereof, wherein the nucleotide corresponding to the nucleotide at position 146 is cytosine and labeled with a fluorescent dye.

Here, the "nucleotide corresponding to the nucleotide at position 146" means, in the complementary or homologous sequence, the complementary nucleotide c which corresponds to g at nucleotide position 146 in SEQ ID NOs:3 and 4. In the P2 probe, this c preferably exists at the first, second or third position from the 5'-end, more preferably exists at the 5'-end.

The probe composed of the oligonucleotide P2 is a probe for detecting a polymorphism at nucleotide position 135 in the nucleotide sequence of SEQ ID NO:3. This nucleotide corresponds to the nucleotide for the T757C mutation, and the nucleotide is T in the case of the wild type, and C in the case of the variant. Sequences of a region containing T757C are shown in SEQ ID NOs:3 (the wild type having T at position 135) and 4 (the variant having C at position 135).

The probe for detection of the polymorphism has a length of preferably 12 to 30 consecutive nucleotides, more preferably 15 to 30 consecutive nucleotides, still more preferably 15 to 25 consecutive nucleotides.

The probe composed of the oligonucleotide P2 may comprise either one or both of an oligonucleotide for detection of the wild type, comprising a nucleotide sequence complementary to a nucleotide sequence of 12 to 50 consecutive nucleotides containing nucleotides 135 to 146 in SEQ ID NO:3 or a homologous sequence thereof, wherein the nucleotide corresponding to the nucleotide at position 146 is cytosine and labeled with a fluorescent dye; and an oligonucleotide for detection of the variant, comprising a nucleotide sequence complementary to a nucleotide sequence of 12 to 50 consecutive nucleotides containing nucleotides 135 to 146 in SEQ ID NO:4 or a homologous sequence thereof, where the nucleotide corresponding to the nucleotide at position 146 is cytosine and labeled with a fluorescent dye.

The probe preferably has the nucleotide sequence of SEQ ID NO:10 described below, which probe is for detection of the variant (the uppercase letter indicates the mutated nucleotide; this provision is also applied hereinafter):

```
5'-*cacctccccgtGctg-3'      (SEQ ID NO: 10)
``` wherein c* indicates c which is fluorescence-labeled at its 5'-side (this provision is also applied hereinafter).

In the corresponding probe for detection of the wild type, the uppercase G is replaced with A.

(P3) An oligonucleotide comprising a nucleotide sequence complementary to a nucleotide sequence of 10 to 50 consecutive nucleotides containing nucleotides 135 to 144 in SEQ ID NO:3 or 4 or a homologous sequence thereof, wherein the nucleotide corresponding to the nucleotide at position 144 is cytosine and labeled with a fluorescent dye.

Here, the "nucleotide corresponding to the nucleotide at position 144" means, in the complementary or homologous sequence, the complementary nucleotide c which corresponds to g at nucleotide position 144 in SEQ ID NOs:3 and 4. In the P3 probe, this c preferably exists at the first, second or third position from the 5'-end, more preferably exists at the 5'-end.

The probe composed of the oligonucleotide P3 is a probe for detecting a polymorphism at nucleotide position 135 in the nucleotide sequence of SEQ ID NO:3.

The probe for detection of the polymorphism has a length of preferably 10 to 30 consecutive nucleotides, more preferably 15 to 25 consecutive nucleotides.

The probe composed of the oligonucleotide P3 may comprise either one or both of an obligonucleotide for detection of the wild type, comprising a nucleotide sequence complementary to a nucleotide sequence of 10 to 50 consecutive nucleotides containing nucleotides 135 to 144 in SEQ ID NO:3 or a homologous sequence thereof, wherein the nucleotide corresponding to the nucleotide at position 144 is cytosine and labeled with a fluorescent dye; and an oligonucleotide for detection of the variant, comprising a nucleotide sequence complementary to a nucleotide sequence of 10 to 50 consecutive nucleotides containing nucleotides 135 to 144 in SEQ ID NO:4 or a homologous sequence thereof, wherein the nucleotide corresponding to the nucleotide at position 144 is cytosine and labeled with a fluorescent dye.

The probe preferably has the nucleotide sequence of SEQ ID NO:11 described below, which probe is for detection of the variant:

```
5'-*cctccccgtGctggc-3'.      (SEQ ID NO: 11)
```

In the corresponding probe for detection of the wild type, the uppercase G is replaced with A.

(P3') An oligonucleotide comprising a nucleotide sequence complementary to a nucleotide sequence of 10 to 50 consecutive nucleotides containing nucleotides 142 to 144 in SEQ ID NO:3 or 5 or a homologous sequence thereof, wherein the nucleotide corresponding to the nucleotide at position 144 is cytosine and labeled with a fluorescent dye.

Here, the "nucleotide corresponding to the nucleotide at position 144" means, in the complementary or homologous sequence, the complementary nucleotide c which corresponds to g at nucleotide position 144 in SEQ ID NOs:3 and 5. In the P3' probe, this c preferably exists at the first, second or third position from the 5'-end, more preferably exists at the 5'-end.

The probe composed of the oligonucleotide P3' is a probe for detecting a polymorphism at nucleotide position 142 in the nucleotide sequences of SEQ ID NO:3. This nucleotide corresponds to the nucleotide for the A764T mutation, and the nucleotide is A in the case of the wild type, and T in the case of the variant. Sequences of a region containing A764T are shown in SEQ ID NOs:3 (the wild type having A at position 142) and 5 (the variant having T at position 142).

The probe for detection of the polymorphism has a length of preferably 10 to 30 consecutive nucleotides, more preferably 15 to 25 consecutive nucleotides, and the probe may comprise either one or both of an oligonucleotide for detection of the wild type, comprising a nucleotide sequence complementary to a nucleotide sequence of 10 to 50 consecutive nucleotides containing nucleotides 142 to 144 in SEQ ID NO:3 or a homologous sequence thereof, wherein the nucleotide corresponding to the nucleotide at position 144 is cytosine and labeled with a fluorescent dye; and an oligonucleotide for detection of the variant, comprising a nucleotide sequence complementary to a nucleotide sequence of 10 to 50 consecutive nucleotides containing nucleotides 142 to 144 in SEQ ID NO:5 or a homologous sequence thereof, wherein the nucleotide corresponding to the nucleotide at position 144 is cytosine and labeled with a fluorescent dye.

The probe preferably has the nucleotide sequence of SEQ ID NO:16 described below, which probe is for detection of the variant:

```
5'-*ccAccccgtactggcc-3'.     (SEQ ID NO: 16)
```

In the corresponding probe for detection of the wild type, the uppercase A is replaced with T.

(P4) An oligonucleotides comprising a nucleotide sequence complementary to a nucleotide sequence of 10 to 50 consecutive nucleotides containing nucleotides 134 to 135 in SEQ ID NO:3 or 4 or a homologous sequence thereof, wherein the nucleotide corresponding to the nucleotide at position 134 is cytosine and labeled with a fluorescent dye.

Here, the "nucleotide corresponding to the nucleotide at position 134" means, in the complementary or homologous sequence, the complementary nucleotide c which corresponds to g at nucleotide position 134 in SEQ ID NOs:3 and 4. In the P4 probe, this c preferably exists at the first, second or third position from the 3'-end, more preferably exists at the 3'-end.

The probe composed of the oligonucleotide P4 is a probe for detecting a polymorphism at nucleotide position 135 in the nucleotide sequence of SEQ ID NO:3.

The probe for detection of the polymorphism has a length of preferably 10 to 30 consecutive nucleotides, more preferably 15 to 25 consecutive nucleotides.

The probe composed of the oligonucleotide P4 may comprise either one or both of an oligonucleotide for detection of the wild type, comprising a nucleotide sequence complementary to a nucleotide sequence of 10 to 50 consecutive nucleotides containing nucleotides 134 to 135 in SEQ ID NO:3 or a homologous sequence thereof, wherein the nucleotide corresponding to the nucleotide at position 134 is cytosine and labeled with a fluorescent dye; and an oligonucleotide for detection of the variant, comprising a nucleotide sequence complementary to a nucleotide sequence of 10 to 50 consecutive nucleotides containing nucleotides 134 to 135 in SEQ ID NO:4 or a homologous sequence thereof, wherein the nucleotide corresponding to the nucleotide at position 134 is cytosine and labeled with a fluorescent dye.

The probe preferably has the nucleotide sequence of SEQ ID NO:12 described below, which probe is for detection of the variant:

```
5'-gtacacctccccgtGc*-3'.     (SEQ ID NO: 12)
```

In the corresponding probe for detection of the wild type, the uppercase G is replaced with A.

(P5) An oligonucleotide comprising a nucleotide sequence complementary to a nucleotide sequence of 10 to 50 consecutive nucleotides containing nucleotides 138 to 142 in SEQ ID NO:3 or 5 or a homologous sequence thereof, wherein the nucleotide corresponding to the nucleotide at position 138 is cytosine and labeled with a fluorescent dye.

Here, the "nucleotide corresponding to the nucleotide at position 138" means, in the complementary or homologous sequence, the complementary nucleotide c which corresponds to g at nucleotide position 138 in SEQ ID NOs:3 and 5. In the P5 probe, this c preferably exists at the first, second or third position from the 3'-end, more preferably exists at the 3'-end.

The probe composed of the oligonucleotide P5 is a probe for detecting a polymorphism at nucleotide position 142 in the nucleotide sequence of SEQ ID NO:3.

The probe for detection of the polymorphism has a length of preferably 10 to 30 consecutive nucleotides, more preferably 15 to 25 consecutive nucleotides.

The probe composed of the oligonucleotide P5 may comprise either one or both of an oligonucleotide for detection of the wild type, comprising a nucleotide sequence complementary to a nucleotide sequence of 10 to 50 consecutive nucleotides containing nucleotides 138 to 142 in SEQ ID NO:3 or a homologous sequence thereof, wherein the nucleotide corresponding to the nucleotide at position 138 is labeled with a fluorescent dye; and an oligonucleotide for detection of the variant, comprising a nucleotide sequence complementary to a nucleotide sequence of 10 to 50 consecutive nucleotides containing nucleotides 138 to 142 in SEQ ID NO:5 or a homologous sequence thereof, wherein the nucleotide corresponding to the nucleotide at position 138 is cytosine and labeled with a fluorescent dye.

The probe preferably has the nucleotide sequence of SEQ ID NO:13 described below, which probe is for detection of the variant:

```
5'-cctcgtacaccAcccc*-3'.     (SEQ ID NO: 13)
```

In the corresponding probe for detection of the wild type, the uppercase A is replaced with T.

(P6) An oligonucleotide comprising a nucleotide sequence complementary to a nucleotide sequence of 12 to 50 consecutive nucleotides containing nucleotides 142 to 153 in SEQ ID NO:3 or 5 or a homologous sequence thereof, wherein the nucleotide corresponding to the nucleotide at position 153 is cytosine and labeled with a fluorescent dye.

Here, the "nucleotide corresponding to the nucleotide at position 153" means, in the complementary or homologous sequence, the complementary nucleotide c which corresponds to g at nucleotide position 153 in SEQ ID NOs:3 and 5. In the P6 probe, this c preferably exists at the first, second or third position from the 5'-end, more preferably exists at the 5'-end.

The probe composed of the oligonucleotide P6 is a probe for detecting a polymorphism at nucleotide position 142 in the nucleotide sequence of SEQ ID NO:3.

The probe for detection of the polymorphism has a length of preferably 12 to 30 consecutive nucleotides, more preferably 15 to 30 consecutive nucleotides, still more preferably 15 to 25 consecutive nucleotides.

The probe composed of the oligonucleotide P6 may comprise either one or both of an oligonucleotide for detection of the wild type, comprising a nucleotide sequence complementary to a nucleotide sequence of 12 to 50 consecutive nucleotides containing nucleotides 142 to 153 in SEQ ID NO:3 or a homologous sequence thereof, wherein the nucleotide corresponding to the nucleotide at position 153 is cytosine and labeled with a fluorescent dye; and an oligonucleotide for detection of the variant, comprising a nucleotide sequence complementary to a nucleotide sequence of 12 to 50 consecutive nucleotides containing nucleotides 142 to 153 in SEQ ID NO:5 or a homologous sequence thereof, wherein the nucleotide corresponding to the nucleotide at position 153 is cytosine and labeled with a fluorescent dye.

The probe preferably has the nucleotide sequence of SEQ ID NO:14 described below, which probe is for detection of the variant:

```
5'-*cctcgtacaccAcccc-3'.      (SEQ ID NO: 14)
```

In the corresponding probe for detection of the wild type, the uppercase A is replaced with T.

(P7) An oligonucleotide comprising a nucleotide sequence complementary to a nucleotide sequence of 10 to 50 consecutive nucleotides containing nucleotides 142 to 150 in SEQ ID NO:3 or 5 or a homologous sequence thereof, wherein the nucleotide corresponding to the nucleotide at position 150 is cytosine and labeled with a fluorescent dye.

Here, the "nucleotide corresponding to the nucleotide at position 150" means, in the complementary or homologous sequence, the complementary nucleotide c which corresponds to g at nucleotide position 150 in SEQ ID NOs:3 and 5. In the P7 probe, this c preferably exists at the first, second or third position from the 5'-end, more preferably exists at the 5'-end.

The probe composed of the oligonucleotide P7 is a probe for detecting a polymorphism at nucleotide position 142 in the nucleotide sequence of SEQ ID NO:3.

The probe for detection of the polymorphism has a length of preferably 10 to 30 consecutive nucleotides, more preferably 15 to 25 consecutive nucleotides.

The probe composed of the oligonucleotide P7 may comprise either one or both of an oligonucleotide for detection of the wild type, comprising a nucleotide sequence complementary to a nucleotide sequence of 10 to 50 consecutive nucleotides containing nucleotides 142 to 150 in SEQ ID NO:3 or a homologous sequence thereof, wherein the nucleotide corresponding to the nucleotide at position 150 is cytosine and labeled with a fluorescent dye; and an oligonucleotide for detection of the variant, comprising a nucleotide sequence complementary to a nucleotide sequence of 10 to 50 consecutive nucleotides containing nucleotides 142 to 150 in SEQ ID NO:5 or a homologous sequence thereof, wherein the nucleotide corresponding to the nucleotide at position 150 is cytosine and labeled with a fluorescent dye.

The probe preferably has the nucleotide sequence of SEQ ID NO:15 described below, which probe is for detection of the variant:

```
5'-*cgtacaccAccccgta-3'.      (SEQ ID NO: 15)
```

In the corresponding probe for detection of the wild type, the uppercase A is replaced with T.

(P8) An oligonucleotide comprising a nucleotide sequence of 10 to 50 consecutive nucleotides containing nucleotides 126 to 135 in one of SEQ ID NOs:6 to 8 or a homologous sequence thereof, wherein the nucleotide corresponding to the nucleotide at position 135 is cytosine and labeled with a fluorescent dye.

Here, the "nucleotide corresponding to the nucleotide at position 135" means, in the sequence, c at nucleotide position 135 in SEQ ID NOs:6 to 8. In the P8 probe, this c preferably exists at the first, second or third position from the 3'-end, more preferably exists at the 3'-end.

The probe composed of the oligonucleotide P8 is a probe for detecting a polymorphism at nucleotide position 126 in the nucleotide sequence of SEQ ID NO:6. This nucleotide corresponds to the nucleotide for the G895C/T mutation, and the nucleotide is G in the case of the wild type, and C or T in the case of a variant. Sequences of a region containing G895C are shown in SEQ ID NO:6 (the wild type having G at position 126), SEQ ID NO:7 (the variant having C at position 126) and SEQ ID NO:8 (the variant having T at position 126).

The probe for detection of the polymorphism has a length of preferably 10 to 30 consecutive nucleotides, more preferably 15 to 25 consecutive nucleotides.

The probe composed of the oligonucleotide P8 may comprise any one, two or three of an oligonucleotide for detection of the wild type, comprising a nucleotide sequence of 10 to 50 consecutive nucleotides containing nucleotides 126 to 135 in SEQ ID NO:6 or a homologous sequence thereof, wherein the nucleotide corresponding to the nucleotide at position 135 is cytosine and labeled with a fluorescent dye;

an oligonucleotide for detection of a variant, comprising a nucleotide sequence of 10 to 50 consecutive nucleotides containing nucleotides 126 to 135 in SEQ ID NO:7 or a homologous sequence thereof, wherein the nucleotide corresponding to the nucleotide at position 135 is cytosine and labeled with a fluorescent dye; and an oligonucleotide for detection of a variant, comprising a nucleotide sequence of 10 to 50 consecutive nucleotides containing nucleotides 126 to 135 in SEQ ID NO:8 or a homologous sequence thereof, wherein the nucleotide corresponding to the nucleotide at position 135 is cytosine and labeled with a fluorescent dye.

The probe preferably has the nucleotide sequence of SEQ ID NO:17 or 19 described below, which probe is for detection of a variant:

```
5'-cctgCtgcagctcc*-3';       (SEQ ID NO: 17)
or
5'-aacctgTtgcagctcc*-3'.     (SEQ ID NO: 19)
```

In the corresponding probe for detection of the wild type, the uppercase C or T is replaced with G.

(P9) An oligonucleotide comprising a nucleotide sequence of 10 to 50 consecutive nucleotides containing nucleotides 126 to 129 in one of SEQ ID NOs:6 to 8 or a homologous sequence thereof, wherein the nucleotide corresponding to the nucleotide at position 129 is cytosine and labeled with a fluorescent dye.

Here, the "nucleotide corresponding to the nucleotide at position 129" means, in the sequence, c at nucleotide position 129 in SEQ ID NOs:6 to 8. In the P9 probe, this c preferably exists at the first, second or third position from the 3'-end, more preferably exists at the 3'-end.

The probe composed of the oligonucleotide P9 is a probe for detecting a polymorphism at nucleotide position 126 in the nucleotide sequence of SEQ ID NO:6.

The probe for detection of the polymorphism has a length of preferably 10 to 30 consecutive nucleotides, more preferably 15 to 25 consecutive nucleotides.

The probe composed of the oligonucleotide P9 may comprise any one, two or three of an oligonucleotide for detection of the wild type, comprising a nucleotide sequence of 10 to 50 consecutive nucleotides containing nucleotides 126 to 129 in SEQ ID NO:6 or a homologous sequence thereof, wherein the nucleotide corresponding to the nucleotide at position 129 is Cytosine and labeled with fluorescent dye;

an oligonucleotide for detection of a variant, comprising a nucleotide sequence of 10 to 50 consecutive nucleotides containing nucleotides 126 to 129 in SEQ ID NO:7 or a homologous sequence thereof, wherein the nucleotide corresponding to the nucleotide at position 129 is cytosine and labeled with a fluorescent dye; and an oligonucleotide for detection of a variant, comprising a nucleotide sequence of 10 to 50 consecutive nucleotides containing nucleotides 126 to 129 in SEQ ID NO:8 or a homologous sequence thereof, wherein the nucleotide corresponding to the nucleotide at position 129 is cytosine and labeled with a fluorescent dye.

The probe preferably has the nucleotide sequence of SEQ ID NO:18 or 20 described below, which probe is for detection of a variant:

```
5'-accctaacctgctgc*-3';            (SEQ ID NO: 18)
or
5'-tcaaacaccctaacctgTgc*-3'.       (SEQ ID NO: 20)
```

In the corresponding probe for detection of the wild type, the uppercase C or T is replaced with G.

The term "homologous" herein means, in a particular nucleotide sequence, a nucleotide sequence having a sequence having a homology of not less than 80%, more preferably not less than 90%, most preferably not less than 95% to the complementary strand of the nucleotide sequence or to the nucleotide sequence.

The probe of the present invention is preferably a fluorescence-labeled oligonucleotide probe which emits fluorescence when it is not hybridized with a target sequence and whose fluorescence intensity decreases (the fluorescence is quenched) or increases when it is hybridized with the target sequence. Among these, a fluorescence-labeled oligonucleotide probe with emits fluorescene when it is not hybridized with a target sequence and whose fluorescence intensity decreases when it is hybridized with the target sequence is more preferred. Such a probe using the quenching phenomenon is generally called guanine quenching probe, and known as the so called QProbe (registered trademark). Among these, a probe prepared by designing an oligonucleotide such that it has C at the 3'-end or the 5% end and labeling the C at the end with a fluorescent dye such that the emission is decreased when the C is close to 0 is preferred.

In the present specification, when the term "first, second or third position from the 5'-end" is mentioned, the 5'-end is counted as the first position, and, when the term "first, second or third position from the 3'-end" is mentioned, the 3'-end is counted as the first position.

The fluorescent dye is not restricted, and examples thereof include fluorescein, phosphor, rhodamine, and polymethine dye derivatives. Examples of commercially available fluorescent dyes include BODIPY FL (trademark; manufactured by Molecular Probes), FluorePrime (trade name; manufactured by Amersham Pharmacia), Fluoredite (trade name; manufactured by Millipore), FAM (manufactured by ABI), Cy3 and Cy5 (manufactured by Amersham Pharmacia) and TARMA (manufactured by Molecular Probes). The conditions for detection using the probe is not restricted, and may be appropriately determined depending on the fluorescent dye used. The detection may be carried out, for example, with a detection wavelength of 445 to 480 nm in the case of Pacific Blue, with a detection wavelength of 585 to 700 nm in the case of TAMRA, and with a detection wavelength of 520 to 555 nm in the case of BODIPY FL. By using such a probe, hybridization and dissociation can be easily confirmed based on fluctuation of the signal.

Further, the probe of the present invention may have a phosphate group added at the 3'-end. As mentioned later, the DNA to be subjected to detection of the presence/absence of a mutation (target DNA) can be prepared by a gene amplification method such as PCR, and the probe of the present invention may be made to coexist in the reaction liquid for the gene amplification reaction during the preparation. In such cases, by adding a phosphate group to the 3'-end of the probe, extension of the probe itself by the gene amplification reaction can be sufficiently prevented. Further, also by adding a labeling substance as mentioned above to the 3'-end, a similar effect can be obtained.

Table 1 below shows particular examples of probes having the above-described nucleotide sequences, each of which has C at the 5'-end or the 3'-end labeled with a fluorescent dye (the nucleotides represented by uppercase letters represent points of mutation, and P represents a phosphate group). However, the probe of the present invention is not restricted to the followings.

TABLE 1

|  | SEQ ID NO | Sequence |
| --- | --- | --- |
| P1 | SEQ ID NO: 9 | cctgtggatgCagtttttc-(TAMRA) |
| P2 | SEQ ID NO: 10 | (TAMRA)-cacctccccgtGctg-P |
| P3 | SEQ ID NO: 11 | (TAMRA)-cctccccgtGctggc-P |
| P4 | SEQ ID NO: 12 | gtacacctccccgtGc-(TAMRA) |
| P5 | SEQ ID NO: 13 | cctcgtacaccAcccc-(TAMRA) |
| P6 | SEQ ID NO: 14 | (TAMRA)-cctcgtacaccAcccc-P |
| P7 | SEQ ID NO: 15 | (TAMRA)-cgtacaccAccccgta-P |
| P3' | SEQ ID NO: 16 | (TAMRA)-ccAccccgtactggcc-P |
| P8 | SEQ ID NO: 17 | cctgCtgcagctcc-(BODIPY FL) |

TABLE 1-continued

| | SEQ ID NO | Sequence |
|---|---|---|
| P9 | SEQ ID NO: 18 | accctaacctgCtgc-(BODIPY FL) |
| P8 | SEQ ID NO: 19 | aacctgTtgcagctcc-(TAMRA) |
| P9 | SEQ ID NO: 20 | tcaaacaccctaacctgTtgc-(TAMRA) |

The probe of the present invent can be used for detection of a polymorphism in the ab1 gene. The detection method is not restricted as long as it is a method using hybridization between a sequence to be detected and a probe. As one example of the method to which the probe of the present invention is applied, a method for detecting a polymorphism using Tm analysis is described below.

<Method for Detecting Polymorphism>

The method of the present invention for detecting a polymorphism is a method for detecting a polymorphism in the ab1 gene as mentioned above, and comprises the following Steps (I) to (IV). The method of the present invention for detecting a polymorphism is characterized by the use of the probe of the present invention, and other constitutions and conditions are not restricted by the following description.

(I) bringing the probe of the present invention into contact with a sample containing DNA to allow the probe to hybridize with the DNA;

(II) measuring fluctuation of a signal from the hybrid-forming body between the DNA and the probe, which fluctuation occurs due to temperature change;

(III) determining the Tm value by analyzing the fluctuation of the signal; and (IV) determining the presence/absence of the polymorphism of interest or the abundance ratio of a nucleotide sequence(s) having the polymorphism, based on the Tm value.

The determination of the Tm value in Step (III) includes not only determination of the temperature of Tm but also determination of the height of the peak of Tm. Based on the height of the peak, the abundance ratio of a nucleotide sequence(s) having a polymorphism can be determined. For more quantitative determination of the abundance ratio of a nucleotide sequence(s) having a polymorphism, it is preferred to prepare a calibration curve as shown below and determine the abundance ratio based on the prepared calibration curve.

The method of quantitative determination of the abundance ratio of a nucleotide sequence(s) having a polymorphism is shown below by way of an example of determination of the abundance ratios of the wild type and a particular variant. However, this is only an example, and the method of determination of the abundance ratio of a nucleotide sequence(s) having a polymorphism is not restricted thereto.

First, plural nucleic acid mixtures in which two types of nucleic acids, that is, the wild-type nucleic acid Wt and a variant nucleic acid Mt, are contained at various abundance ratios are prepared, and a melting curve is obtained for each of the plural nucleic acid mixtures using a melting curve analysis device or the like.

FIG. 1(A) shows a melting curve represented as the relationship between the temperature and the fluorescence intensity for a certain nucleic acid mixture, and FIG. 1(B) shows a melting curve represented as the relationship between the temperature and the differential value of the fluorescence intensity (also referred to as a differential melting curve). By detecting a peak from this differential melting curve, $Tm_W$, which is the melting temperature of the nucleic acid Wt, and $Tm_M$, which is the melting temperature of the nucleic acid Mt, are detected, and each of the temperature ranges including $Tm_W$ and $Tm_M$ are set. For example, as $\Delta T_w$, which is the temperature range including $Tm_W$, the temperature range whose lower limit is the temperature at which the differential value of the fluorescence intensity is minimum between $Tm_W$ and $Tm_M$ and whose upper limit is the temperature corresponding to the skirt of the peak of the fluorescence intensity can be set. Further, for example, as $\Delta T_M$, which is the temperature range including $Tm_M$, the temperature range whose upper limit is the temperature at which the differential value of the fluorescence intensity is minimum between $Tm_W$ and $Tm_M$ whose lower limit is the temperature corresponding to the skirt of the peak of the fluorescence intensity can be set. The temperature range $\Delta T_w$ and the temperature range ATM may be set such that these have either the same width (e.g., 10° C.) or different widths (e.g., a temperature range $\Delta T$, of 10° C. and a temperature range $\Delta T_M$ of 7° C.). Further, the temperature range $\Delta T_w$ and the temperature range $\Delta T_M$ may be set such that each of these has a width ranging from X° C. higher than the melting temperature Tm to X° C. lower than the melting temperature Tm (e.g., X° C. is not more than 15° C., preferably not more than 10° C.).

Subsequently, for each of the temperature range $\Delta T_w$ and the temperature range $\Delta T_M$, the area surrounded by the line passing through the point corresponding to the lower limit and the point corresponding to the upper limit of the temperature range of the differential melting curve, and the differential melting curve (shaded portion in FIG. 1(B)) is calculated. More particularly, for example, the area can be calculated as follows. By defining the differential value of the fluorescence intensity at temperature T as f(T) and the base value at temperature T as B(T), the area is calculated by the Equation (I) below.

$$\text{Area } S = \{f(T_{s+1}) - B(T_{+1})\} + \{f(T_{s+2})\} + \ldots + \{f(T_{e-1}) - B(T_{e-1})\} \quad (1)$$

In the equation, $T_s$ represents the lower limit value of each temperature range, and $T_e$ represents the upper limit value. The base value B(T) at each temperature T is a value calculated by the Equation (2) below and represents the background level contained in the detection signal of the fluorescence intensity. By subtracting this base value from the differential value of the fluorescence intensity, the effect of the background contained in the detection signal of the fluorescence intensity is removed.

$$B(T) = a \times (T - T_s + f(T_s)) \quad (2)$$

In this equation, $$a = \{f(T_e) - f(T_s)\} / (T_e - T_s).$$

Figure 2:
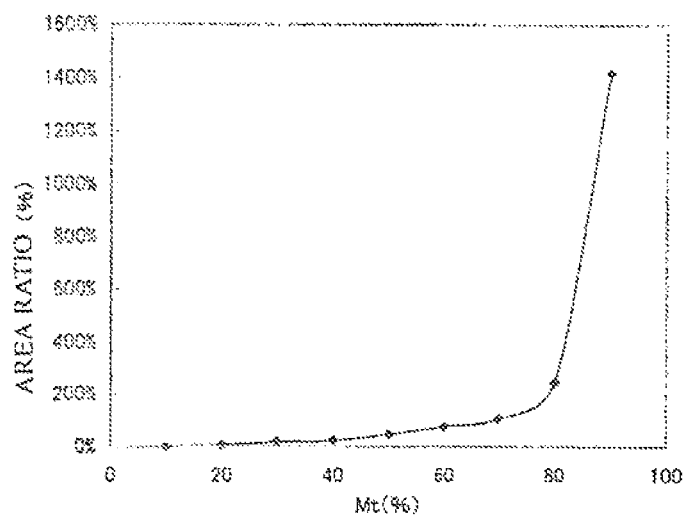
FIG. 2 is a diagram showing an example of a calibration curve.

According to the above Equation (1) and Equation (2) the area $S_w$ in the temperature range $\Delta T_W$ and the area $S_M$ in the temperature range $\Delta T_W$ are calculated, to prepare a calibration curve representing the relationship between the area ratio and the abundance ratio of each nucleic acid mixture. FIG. 2 shows an example of the calibration curve prepared by taking the abundance ratio (the ratio of nucleic acid Mt with respect to the total amount of the nucleic acid mixture) along the abscissa and the area ratio ($S_M/S_W$) along the ordinate. The area ratio may also be defined as $S_W/S_M$.

By calculating the area ratio from the melting curve and the differential melting curve obtained using an actual sample and preliminarily preparing a calibration curve as described above, the abundance ratio of a nucleotide sequence(s) having a polymorphism contained in the actual sample can be determined based on the prepared calibration curve.

In the present invention, the DNA in the sample may be either single-stranded DNA or a double-stranded DNA. In cases where the DNA is double-stranded DNA, for example, the step of dissociating the double-stranded DNA in the sample by heating is preferably included before the hybridization step. By dissociating the double-stranded DNA into single-stranded DNA, hybridization with the detection probe is possible in the subsequent hybridization step.

In the present invention, the DNA contained in the sample may be, for example, DNA originally included in a biological sample, but, in view of enhancement of the detection accuracy, the DNA is preferably an amplification product prepared by amplifying a region containing the site of mutation in the abl gene by PCR or the like using DNA originally contained in a biological sample. The length of the amplification product is not restricted and, for example 50 to 1000 mer, preferably 80 to 200 mer. The DNA in the sample mar also be cDNA synthesized from, for example, RNA (total RNA, mRNA or the like) derived from a biological sample by RT-PCR (Reverse Transcription PCR).

Examples of the sample to which the method of the present invention for detecting a polymorphism is applied include samples wherein the abl gene exists. Particular examples thereof include blood cell samples such as leukocytes and whole blood samples. In the present invention, the method of collection of the sample, the method of preparation of DNA and the like are not restricted, and known methods may be employed therefor.

In the present invention, the ratio (molar ratio) of the probe of the present invention to be added with respect to DNA in the sample is not restricted, and the ratio is preferably not more than 1, more preferably not more than 0.1 with respect to DNA in the sample in view of securing a sufficient detection signal. In this case, for example, the DNA in the sample may be either the total of DNA having the polymorphism to be detected and DNA to be undetected which does not have the polymorphism, or the total of the amplification product containing the sequence to be detected having the polymorphism to be detected and the amplification product containing the sequence to be undetected which does not have the polymorphism. Although the ratio of the DNA to be detected in the DNA in the sample is usually not known, the ratio (molar ratio) of the probe to be added with respect to the DNA to be detected (the amplification product containing the sequence to be detected) is preferably not more than 10, more preferably not more than 5, still more preferably not more than 3 as a result. The lower limit of the ratio is not restricted, and the ratio is, for example, not less than 0.001, preferably not less than 0.01, more preferably not less than 0.1.

The ratio of the probe of the present invention to be added with respect to the DNA may be, for example, either a molar ratio with respect to double-stranded DNA or a molar ratio with respect to single-stranded DNA.

The Tm value will now be described. Heating a solution containing double-stranded DNA causes increase in the absorbance at 260 nm. This occurs because the hydrogen bond between the both strands of the double-stranded DNA is unraveled by the heat and the double-stranded DNA is dissociated into single-stranded DNAs (melting of DNA). When all the double-stranded DNAs are dissociated into single-stranded DNAs, the absorbance becomes about 1.5 times as large as that observed when the heating was initiated (absorbance for only double-stranded DNA), and by this, completion of the melting can be judged. Based on this phenomenon, the melting temperature Tm can be generally defined as the temperature at which increase in the absorbance reached 50% of the total increase in the absorbance.

In the present invention, measurement of the signal fluctuation due to temperature change for determination of the Tm value can be carried out also by measuring the absorbance at 260 nm based on the above-mentioned principle, but the measurement is preferably carried out based on a signal from the label added to the probe of the present invention, which signal fluctuates depending on the state of hybrid formation between the DNA and the probe. Therefore, as the probe of the present invention, the above-mentioned labeled probe is preferably used. Examples of the labeled probe include a fluorescently labeled oligonucleotide probe which emits fluorescence when it is not hybridized with a target sequence and whose fluorescence intensity decreases (the fluorescence is quenched) when it is hybridized with a target sequence; and a fluorescently labeled oligonucleotide probe which emits fluorescence when it is not hybridized with a target sequence and whose fluorescence intensity increases when it is hybridized with a target sequence. In the case of the former probe, the probe shows no signal or a weak signal when it is forming a hybrid (double-stranded DNA) with the sequence to be detected, while the probe shows a signal or the signal increases when the probe is released by heating. In the case of the latter probe, the probe shows a signal by forming a hybrid (double-stranded DNA) with the sequence to be detected, while the signal decreases (disappears) when the probe is released by heating. Therefore, by detecting change in the signal depending on the label under conditions specific to the signal (absorbance and the like), determination of the progress of melting and the Tm value can be carried out similarly to the case of the measurement of the absorbance at 260 nm. For example, the labeling substance in the labeled probe is as mentioned above, and the probe is preferably a fluorescent dye-labeled probe.

The method of the present invention for detecting a polymorphism is now described by way of an example wherein a labeled probe prepared by labeling with a fluorescent dye is employed as the probe of the present invention. The method of the present invention for detecting a polymorphism is characterized by the use, in itself, of the probe of the present invention, and other processes and conditions are not restricted.

First, genomic DNA is isolated from whole blood. The isolation of genomic DNA from whole blood may be carried out by a known method, and a commercially available genomic DNA isolation kit (trade name: GFX Genomic Blood DNA Purification kit; manufactured by GE Healthcare Bio-Sciences KK) or the like may be used.

Thereafter, a labeled probe is added to the sample containing the isolated genomic DNA. Examples of the labeled probe include QProbe. QProbe is a probe prepared by labeling a cytosine nucleotide at an end of the probe with a fluorescent dye, and this hybridizes with the sequence to be detected to cause interaction between the fluorescent dye and a guanine nucleotide in the sequence to be detected, resulting in decrease in the fluorescence (or quenching). The sequence of the labeled probe is as mentioned above, and may be selected depending on the polymorphism to be detected.

The detection probe may be added to a liquid sample containing the isolated genomic DNA or mixed with the genomic DNA in a solvent. The solvent is not restricted, and examples thereof include buffers including Tris-HCl buffer; solvents containing KCl, $MgCl_2$, $MgSO_4$ or glycerol; and PCR reaction liquids; which are known.

The timing of addition of the detection probe is not restricted, and, for example, in cases where an amplification treatment such as the later-mentioned PCR is carried out, the detection probe may be added to the PCR amplification product after the amplification treatment, or may be added before the amplification treatment. In cases where the detection probe is added before an amplification treatment such as PCR, as described above, it is preferred to add a fluorescent dye and/or a phosphate group to the 3'-end.

Preferably, using the isolated genomic DNA as a template, a sequence(s) containing the site at which the polymorphism to be detected is generated (sequence to be detected and/or sequence to be undetected) is/are amplified by a gene amplification method such as PCR. The gene amplification method is not restricted, and examples thereof include the PCR (Polymerase Chain Reaction) method, NASBA (Nucleic acid sequence based amplification) method, TMA (Transcription-mediated amplification) method and SDA (Strand Displacement Amplification) method, among which the PCR method is preferred. The present invention is described by way of examples using the PCR method, but the present invention is not restricted by this. The conditions for the PCR are not restricted, and the PCR may be carried out by a conventional method.

The sequences of the primers for the PCR are not restricted as long as the sequence to be detected and/or sequence to be undetected (the region with which the probe hybridizes) can be amplified therewith, and the primers may be designed appropriately by a conventional method depending on the sequence of interest. The length of each primer is not restricted, and may be set to a length commonly used (e.g., 10 to 50 mer). The followings are examples of primer sets which may be used for amplification of the sequence to be detected upon use of the P1 to P9 probes. It should be noted that these are only examples, and do not restrict the present invention.

Primer Set for P1 Probe

```
Sense primer
                                SEQ ID NO: 21
5'-ggccggccccgtggtgctgctgtacatg-3'

Antisense primer
                                SEQ ID NO: 22
5'-tccatggcgcaggctgcctg-3'
```

Primer Sets for P2 to P4 Probes

```
Sense primer
                                SEQ ID NO: 23
5'-gacaagtgggagatggaacgc-3'

Antisense primer
                                SEQ ID NO: 24
5'-cacggccaccgtcagg-3'
```

Primer Sets for P8 to P9 Probes

```
Sense primer
                                SEQ ID NO: 25
5'-gaaagaagctgcagtcatgaaagagat-3'

Antisense primer
                                SEQ ID NO: 26
5'-cgcgagaccctctcttcagagc-3'
```

The primer sets for the P5 to P7 probes can also be easily designed based on SEQ ID NO:3.

When the amplification is carried out, the copy number of the DNA (sequence to be detected) contained in the sample can be investigated by monitoring the amplification by real-time PCR. That is, since the ratio of the probe forming a hybrid increases as the DNA (sequence to be detected) is amplified by PCR, the fluorescence intensity fluctuates. By monitoring this fluctuation, the copy number and the abundance ratio of the sequence to be detected (normal DNA or mutant DNA) contained in the sample can be investigated.

Subsequently, dissociation of the obtained PCR amplification product, and hybridization between the single-stranded DNA obtained by the dissociation and the labeled probe are carried out.

The heating temperature in the dissociation step is not restricted as long as it is a temperature at which the amplification product can be dissociated, and examples thereof include 85 to 95° C. The heating time is also not restricted, and it is usually 1 second to 10 minutes, preferably 1 second to 5 minutes.

One hybridization between the dissociated single-stranded DNA and the labeled probe may be carried out, for example, after the dissociation step, by decreasing the temperature to less than the heating temperature in the dissociation step. The temperature condition is 40 to 50° C., for example.

The volume and the concentration of each composition in the reaction liquid for the hybridization step are not restricted. More particularly, the DNA concentration of the reaction liquid is, for example, 0.01 to 1 µM, preferably 0.1 to 0.5 µM, and the concentration of the labeled probe is preferably within the range in which the above-described content with respect to the DNA is satisfied, and, for example, 0.001 to 10 µM, preferably 0.001 to 1 µM.

Thereafter, the hybrid-forming body between the obtained single stranded DNA and the labeled probe is gradually heated, and fluctuation of the signal due to the increase in the temperature is measured. For example, in cases where QProbe is used, the fluorescence is decreased (or the fluorescence is quenched) when the probe is hybridized with the single-stranded DNA, and dissociation of the hybrid-forming body causes emission of the fluorescence. Therefore, for example, the hybrid-forming body, whose fluorescence is decreased (or quenched), may be gradually heated, while measuring the increase in the fluorescence intensity according to the increase in the temperature.

The temperature range in which the fluctuation of the fluorescence intensity is measured is not restricted, and the starting temperature is, for example, from room temperature to 85° C., preferably 25 to 70° C.; and the end temperature is, for example, 40 to 105° C. The rate of increase in the temperature is not restricted and, for example, 0.1 to 20° C./second, preferably 0.3 to 5° C./second.

Subsequently, the fluctuation of the signal is analyzed to determine the Tm value. More particularly, the value (−d the amount of increase in the fluorescence intensity/dt) at each temperature is calculated from the obtained fluorescence intensity, and the temperature at which the value is lowest may be determined as the Tm value. Further, the point at which the amount of increase in the fluorescence intensity per unit time (the amount of increase in the fluorescence intensity/t) is largest may also be determined as the Tm value. In cases where, as the labeled probe, a probe with which the signal intensity increases upon hybrid formation is used solely instead of a quenching probe, the amount of decrease in the fluorescence intensity may be measured instead.

The Tm value may be calculated by the known MELT-CALC software (http://www.meltcalc.com/) or the like, and may also be determined by the Nearest Neighbor Method.

Further, in the present invention, as an alternative to the above-mentioned method wherein the hybrid-forming body is heated while measuring the signal fluctuation according to increase in the temperature, measurement of signal fluctuation upon formation of the hybrid may be carried out, for example. That is, the temperature of the sample to which the probe was added may be decreased to allow formation of the hybrid-forming body while measuring the signal fluctuation according to the decrease in the temperature.

More particularly, for example, in cases where a fluorescently labeled oligonucleotide probe (e.g., QProbe) which emits fluorescence when it is not hybridized with a target sequence and whose fluorescence intensity decreases (whose fluorescence is quenched) when it is hybridized with a target sequence is used, the probe emits fluorescence when the probe is added to the sample since the probe is dissociated at that time, while the fluorescence decreases (or the fluorescence is quenched) upon formation of the hybrid due to decrease in the temperature. Therefore, for example, the temperature of the heated sample may be gradually decreased while measuring decrease in the fluorescence intensity according to the decrease in the temperature.

On the other hand, in cases where a labeled probe whose signal increases upon formation of the hybrid is used, the probe does not emit fluorescence when the probe is added to the sample since the probe is dissociated at that time, while the probe emits fluorescence when the hybrid is formed due to decrease in the temperature. Therefore, for example, the temperature of the sample may be gradually decreased while measuring increase in the fluorescence intensity according to the decrease in the temperature.

By the method of the present invention for detecting a polymorphism in the abl gene, the presence/absence of a mutation related to resistance to an agent for leukemia (e.g., imatinib) can be investigated. Based on the presence/absence of the polymorphism and the abundance ratio between the mutant sequence and the normal sequence, resistance to an antileukemic agent, or a pharmacological effect of an antileukemic agent can be judged. The method of the present invention is useful for determining the therapeutic strategy for leukemia, such as increasing of the dose of an agent, changing to another therapeutic agent, or switching to bone marrow transplantation, based on the presence/absence of the polymorphism and the abundance ratio between the mutant sequence and the normal sequence.

<Reagent Kit for Detection of Polymorphism in abl Gene>

The reagent kit of the present invention for detection of a polymorphism in the abl gene is a reagent kit to be used for detection of a polymorphism in the abl gene, and the reagent kit comprises the probe of the present invention. The reagent kit of the present invention may comprise either one type, or two or more types of the probe(s) of the present invention. In the latter case, the two or more types of the probes may be contained either in the state of a mixture or as separate reagents. Further, in cases where the two or more types of the probes of the present invention are contained in the state of a mixture in the probe kit of the present invention, and in cases where these are contained as separate reagents but used in the same reaction system to carry out Tm analysis of each probe and each sequence to be detected, the respective probes are preferably labeled with different fluorescent substances. By using different types of fluorescent substances like this, detection with the respective probes is possible even in cases where the same reaction system is used. The fluorescent substances are preferably substances having different detection wavelengths.

Further, the reagent kit for detection of a polymorphism in the abl gene may contain a primer set for amplification of a sequence containing the above-described polymorphic site (the region with which the probe hybridizes).

As mentioned above, plural mutations related to leukemia are known for the abl gene, and the probe of the present invention enables detection of the various mutations as mentioned above. In the abl gene involved in leukemia, a mutation at only one site is detected in some cases, but mutations at plural sites are detected in the other cases. Therefore, by detecting plural mutations and comprehensively judging the results, better diagnosis and therapy are possible. Thus, by including two or more types of the probes of the present invention in the reagent kit of the present invention, detection of mutations for diagnosis and therapy can be carried out more simply.

Examples of the present invention will now be described. However, the present invention is not restricted by the Examples below.

EXAMPLE 1

Point Mutation (T→G) at Nucleotide Position 1076 in abl Gene

By using the probe of the present invention, PCR and Tm analysis were carried out for the point mutation (T→G) at nucleotide position 1076 in the abl gene using a fully automatic SNPs testing device (trade name: i-densy (trademark), manufactured by ARKRAY, Inc.).

A plasmid in which the normal abl gene sequence (SEQ ID NO: 1) having no mutation for T at nucleotide position 133 shown in SEQ ID NO:1 was inserted (wtDNA), and a plasmid in which the mutant abl gene (abl tyrosine kinase T1076G (F359C); SEQ ID NO:2) having the mutation from T to G at the nucleotide position 133 was inserted (mtDNA) were mixed together at a predetermined ratio (mtDNA:wtDNA=25 copies:975 copies) (2.5% mutation content), and the resulting mixture was diluted to 1,000 copies/μL, to provide a template nucleic acid. The reaction solution was formulated as shown in Table 2. The PCR reaction was carried out by treatment at 95° C. for 60 seconds, followed by 50 cycles of 95° C. for 1 second and 64° C. for 30 seconds. Thereafter, treatment was further carried out at 95° C. for 1 second and then at 40° C. for 60 seconds, followed by heating the reaction solution from 40° C. to 95° C. at a temperature increase rate of 1° C./3 seconds, while measuring change in the fluorescence intensity with time (WAVE3: 585-700 nm).

TABLE 2

| Reaction liquid volume: 1 × PCR buffer | 50 μl |
|---|---|
| dNTP | 0.2 mM |
| MgCl$_2$ | 1.5 mM |
| Taq polymerase (manufactured by ARKRAY, Inc.) | 1.88 U/test |
| Probe | 0.1 μM |
| Sense primer | 2 μM |
| Antisense primer | 1 μM |
| Template nucleic acid | 4 μl |

```
Sense primer
                                          SEQ ID NO: 21
5'-ggccggccccgtggtgctgctgtacatg-3'

Antisense primer
                                          SEQ ID NO: 22
5'-tccatggcgcaggctgcctg-3'
```

Example 1

```
Detection probe P1
                                    SEQ ID NO: 9
5'-cctgtggatgCagtttttc-(TAMRA)-3'
```

Comparative Example 1

```
Detection probe
                                    SEQ ID NO: 9
5'-(TAMRA)-cctgtggatgCagtttttc-P-3'
```

This probe has the same sequence as that of the detection probe of Example 1, but it is a probe wherein c at the 5'-end (c which is the complementary nucleotide of g at nucleotide position 143 in SEQ ID NO:2) is labeled with a fluorescent dye.

Figure 3A:
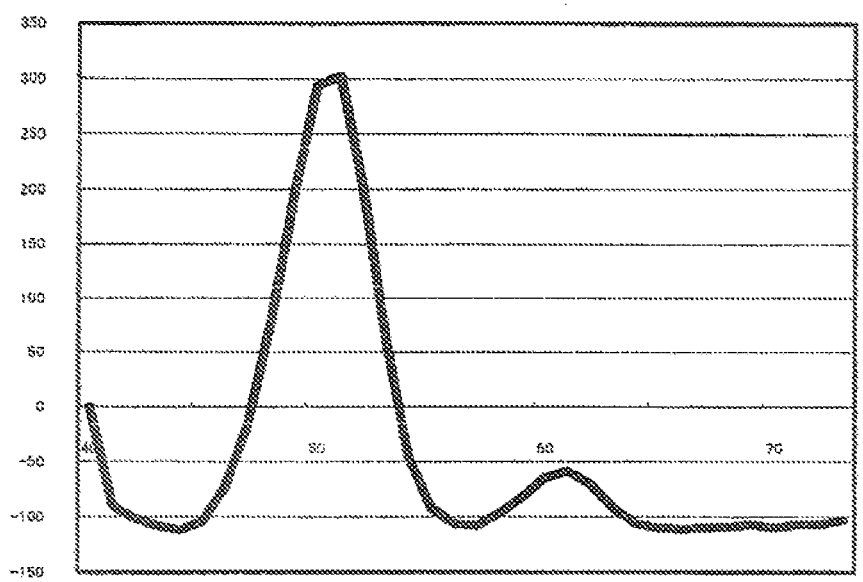
FIG. 3A shows change in the amount of change in the fluorescence intensity of TAMRA per unit time (d the amount of increase in the fluorescence intensity/t) in Tm analysis for the plasmid containing T1076G (F359C) (2.5% mutation content) in Example 1 using the probe of SEQ ID NO:9 (labeled at the 3'-end). The ordinate indicates the amount of change in the fluorescence intensity per unit time (d the amount of increase in the fluorescence intensity/t), and the abscissa indicates the temperature (° C.).

The results are shown in FIG. 3. FIG. 3A is a graph showing the result of Tm analysis, in which change in the fluorescence intensity according to increase in the temperature is shown. As a result of PCR and Tm analysis using the detection probe P1, the peak for wtDNA was observed at about 51° C. and the peak for mtDNA was observed at about 61° C.

From these results, it was revealed that use of the detection probe P1 enables enhancement of the detection sensitivity for mtDNA even in cases where mtDNA and wtDNA coexist.

Figure 3B:
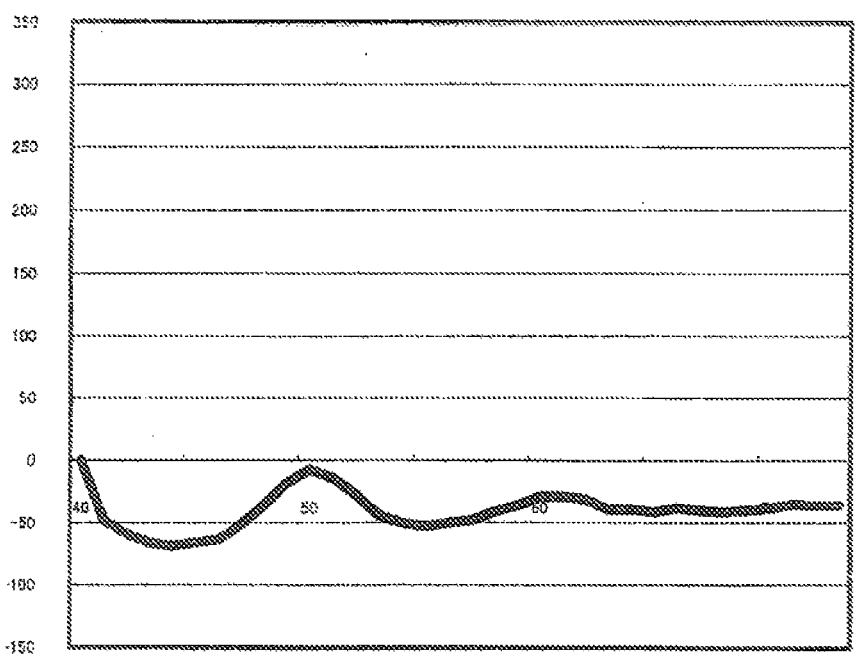
FIG. 3B shows change in the amount of change in the fluorescence intensity of TAMRA per unit time (d the amount of increase in the fluorescence intensity/t) in Tm analysis for the plasmid containing T1076G (F359C) (2.5% mutation content) in Comparative Example 1 using the probe of SEQ ID NO:9 (labeled at the 5'-end). The ordinate indicates the amount of change in the fluorescence intensity per unit time (d the amount of increase in the fluorescence intensity/t), and the abscissa indicates the temperature (° C.).
Figure 4A:
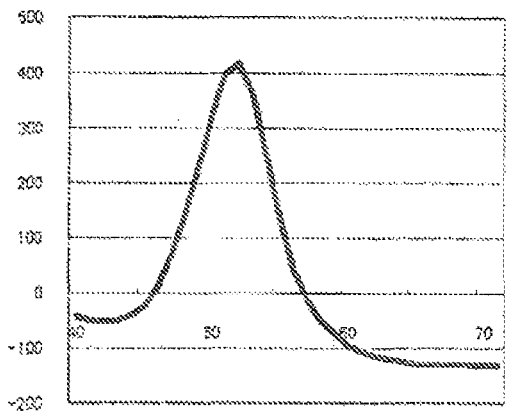
FIG. 4A shows change in the amount of change in the fluorescence intensity of TAMRA per unit time (d the amount of increase in the fluorescence intensity/t) in Tm analysis for the plasmid containing T757C (Y253H) (0% (I), 10% (II) or 20% (III) mutation content) in Example 2-1 using the probe of SEQ ID NO:10. The ordinate indicates the amount of change in the fluorescence intensity per unit time (d the amount of increase in the fluorescence intensity/t), and the abscissa indicates the temperature (° C.).
Figure 4A:
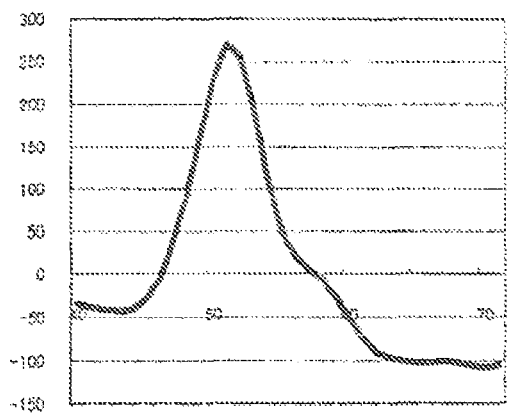
Figure 4A:
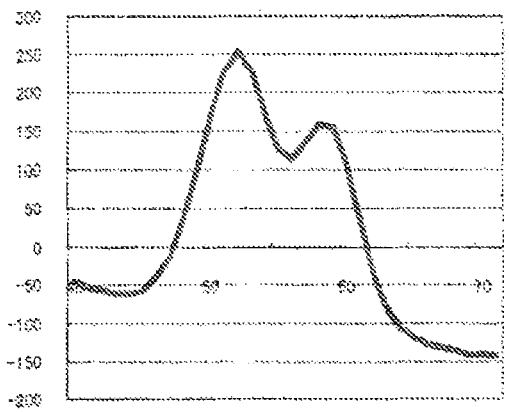
Figure 4B:
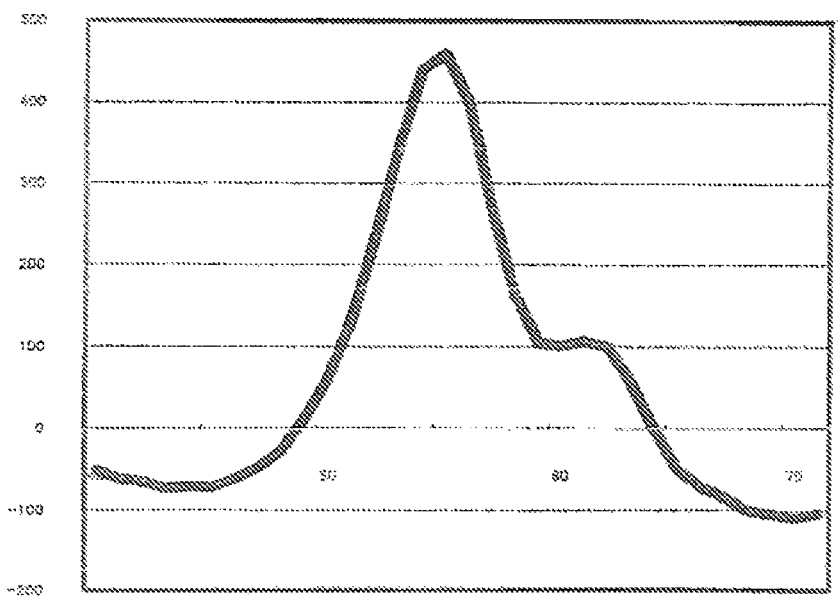
FIG. 4B shows change in the amount of change in the fluorescence intensity of TAMRA per unit time (d the amount of increase in the fluorescence intensity/t) in Tm analysis for the plasmid containing T757C (Y253H) (10% mutation content) in Example 2-2 using the probe of SEQ ID NO:11. The ordinate indicates the amount of change in the fluorescence intensity per unit time (d the amount of increase in the fluorescence intensity/t), and the abscissa indicates the temperature (° C.).
Figure 4C:
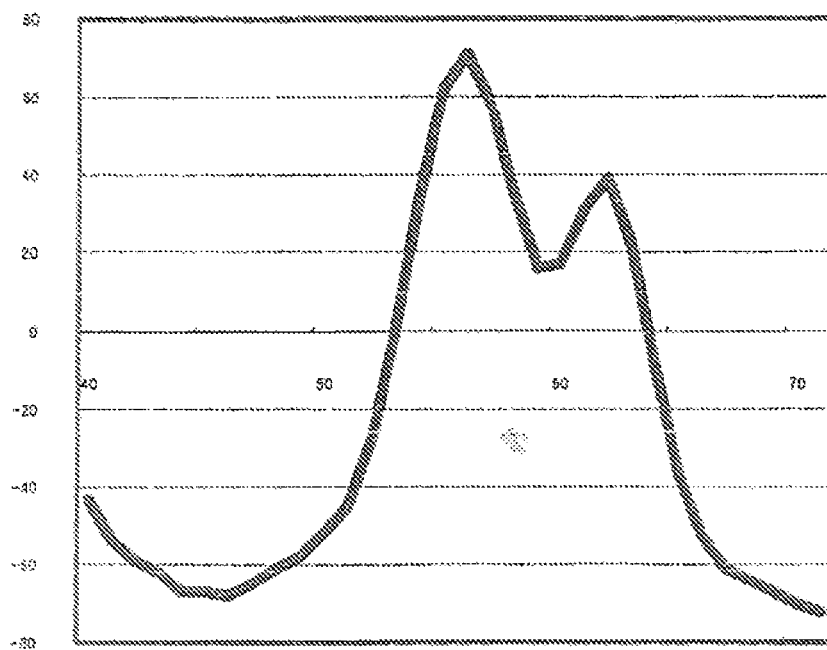
FIG. 4C shows change in the amount of change in the fluorescence intensity of TAMRA per unit time (d the amount of increase in the fluorescence intensity/t) in Tm analysis for the plasmid containing T757C (Y253H) (10% mutation content) in Example 2-3 using the probe of SEQ ID NO:12. The ordinate indicates the amount of change in the fluorescence intensity per unit time (d the amount of increase in the fluorescence intensity/t), and the abscissa indicates the temperature (° C.).
Figure 5A:
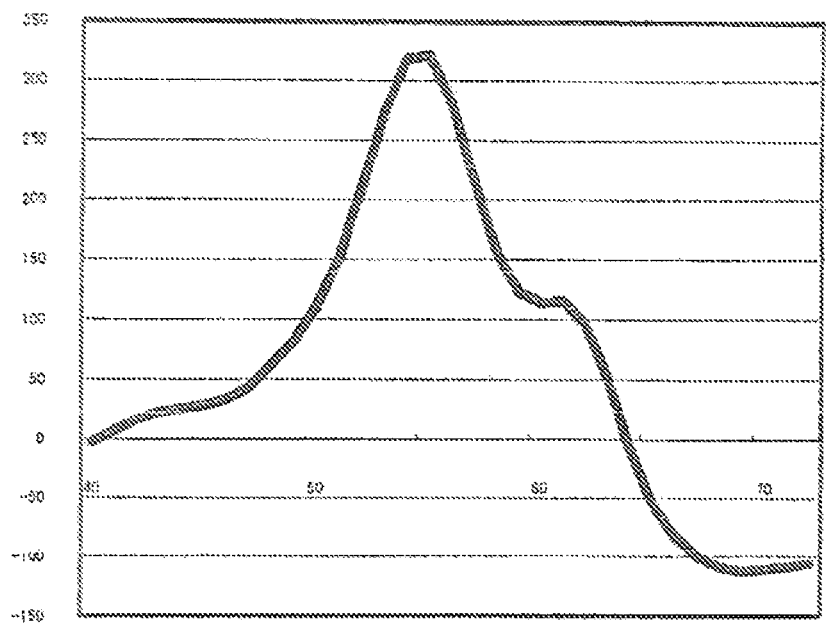
FIG. 5A shows change in the amount of change in the fluorescence intensity of TAMRA per unit time (d the amount of increase in the fluorescence intensity/t) in Tm analysis for the strand complementary to the probe containing A764T (E255V) (10% mutation content) in Example 3-1 using the probe of SEQ ID NO:13. The ordinate indicates the amount of change in the fluorescence intensity per unit time (d the amount of increase in the fluorescence intensity/t), and the abscissa indicates the temperature (° C.).
Figure 5B:
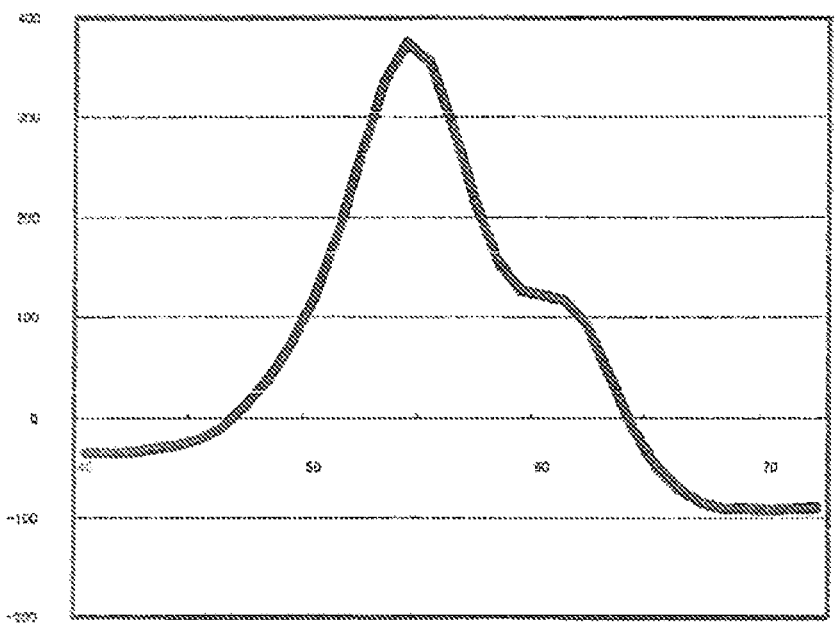
FIG. 5B shows change in the amount of change in the fluorescence intensity of TAMRA per unit time (d the amount of increase in the fluorescence intensity/t) in Tm analysis for the strand complementary to the probe containing A764T (E255V) (10% mutation content) in Example 3-2 using the probe of SEQ ID NO:14. The ordinate indicates the amount of change in the fluorescence intensity per unit time (d the amount of increase in the fluorescence intensity/t), and the abscissa indicates the temperature (° C.).
Figure 5C:
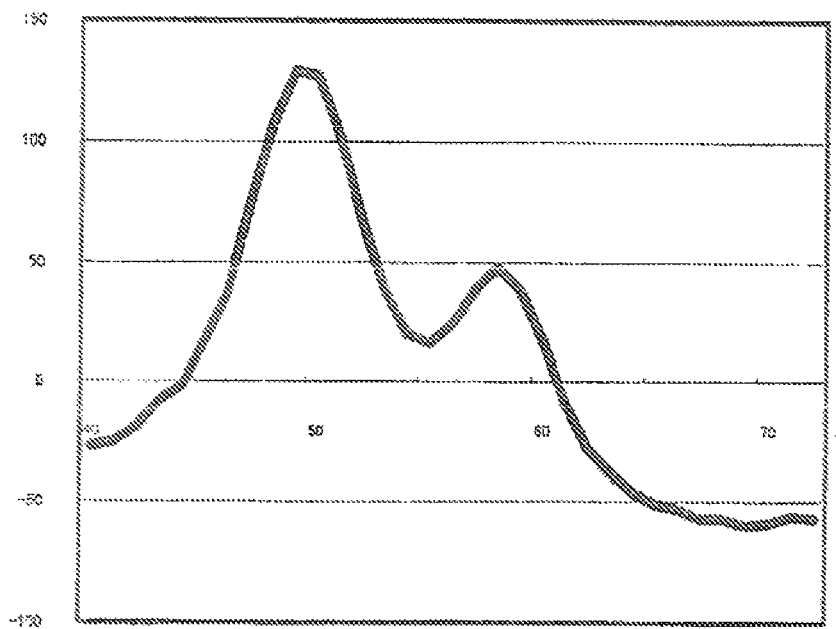
FIG. 5C shows change in tip change in the fluorescence intensity of TAMRA per unit time (d the amount of increase in the fluorescence intensity/t) in Tm analysis for the strand complementary to the probe containing A764T (E255V) (10% mutation content) in Example 3-3 using the probe of SEQ ID NO:15. The ordinate indicates the amount of change in the fluorescence intensity per unit time (d the amount of increase in the fluorescence intensity/t), and the abscissa indicates the temperature (° C.).
Figure 5D:
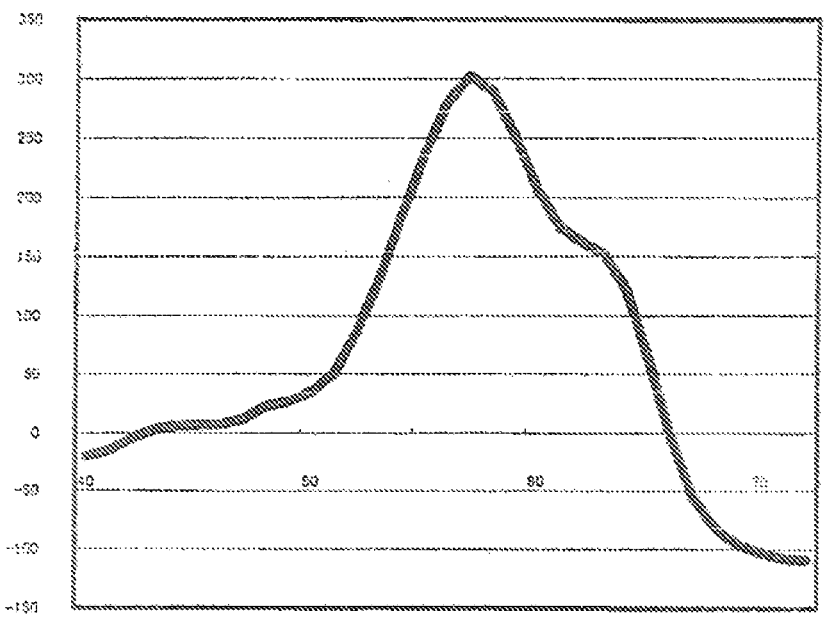
FIG. 5D shows change in the amount of change in the fluorescence intensity of TAMRA per unit time (d the amount of increase in the fluorescence intensity/t) in Tm analysis for the strand complementary to the probe containing A764T (E255V) (10% mutation content) in Example 3-4 using the probe of SEQ ID NO:16. The ordinate indicates the amount of change in the fluorescence intensity per unit time (d the amount of increase in the fluorescence intensity/t), and the abscissa indicates the temperature (° C.).
Figure 6A:
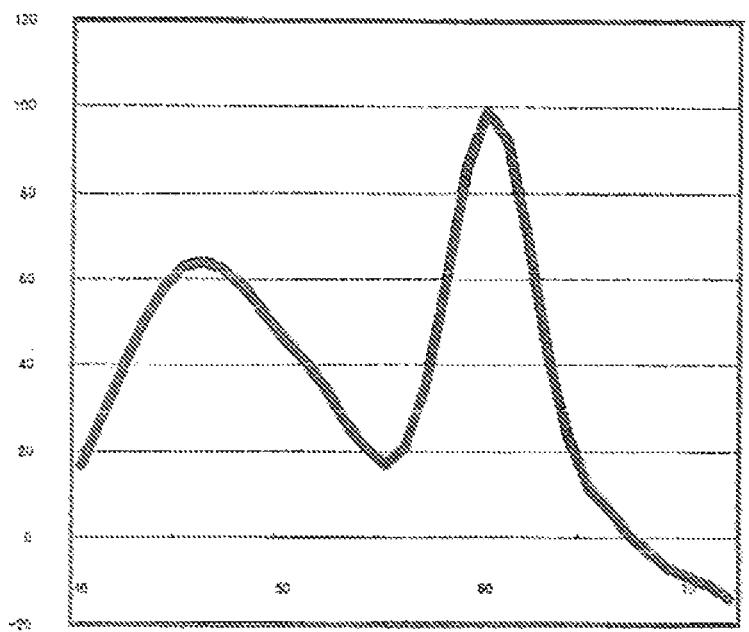
FIG. 6A shows change in the amount of change in the fluorescence intensity of BODIPY FL per unit time (d the amount of increase in the fluorescence intensity/t) in Tm analysis for the plasmid containing G895C (V299L) (5% mutation content) in Example 4-1 using the probe of SEQ ID NO:17. The ordinate indicates the amount of change in the fluorescence intensity per unit time (d the amount of increase in the fluorescence intensity/t), and the abscissa indicates the temperature (° C.).
Figure 6B:
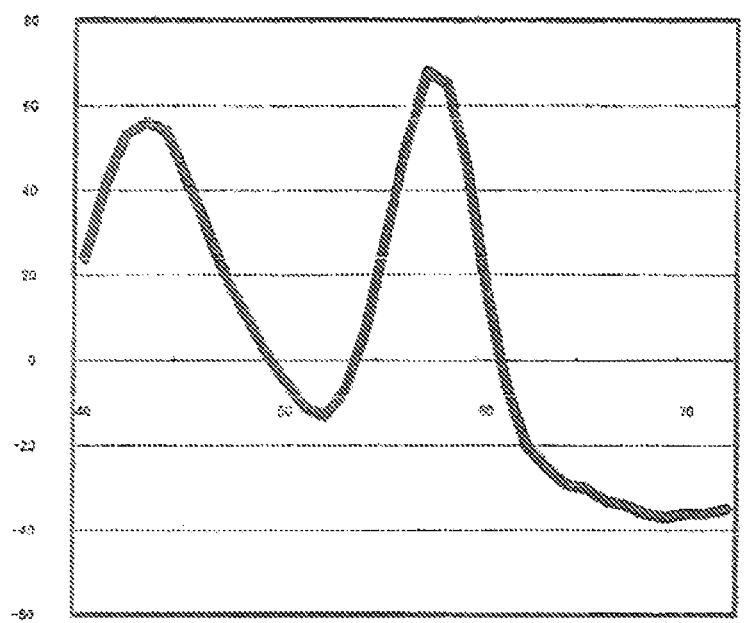
FIG. 6B shows change in the amount of change in the fluorescence intensity of BODIPY FL per unit time (d the amount of increase in the fluorescence intensity/t) in Tm analysis for the plasmid containing G895C (V299L) (5% mutation content) in Example 4-2 using the probe of SEQ ID NO:18. The ordinate indicates the amount of change in the fluorescence intensity per unit time (d the amount of increase in the fluorescence intensity/t), and the abscissa indicates the temperature (° C.).
Figure 6C:
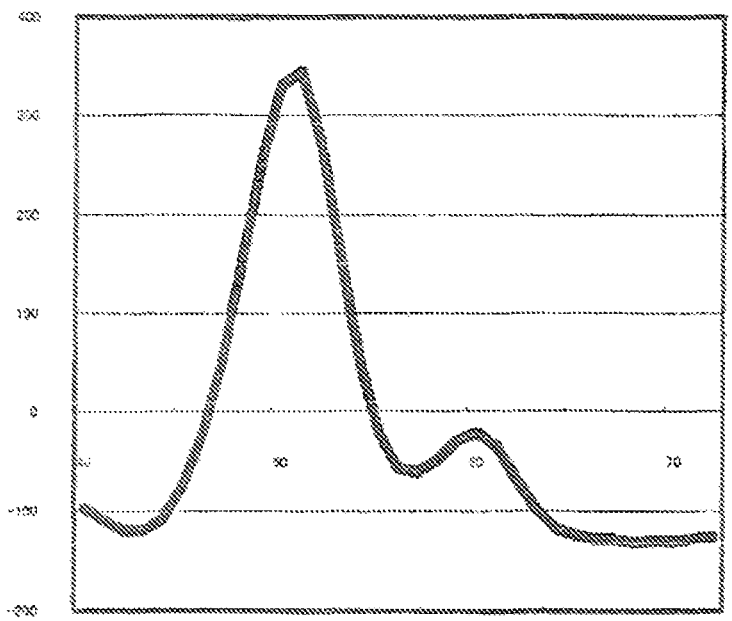
FIG. 6C shows change in the amount of change in the fluorescence intensity of TAMRA per unit time (d the amount of increase in the fluorescence intensity/t) in analysis for the plasmid containing G895T (V299L) (5% mutation content) in Example 4-3 using the probe of SEQ ID NO:19. The ordinate indicates the amount of change in the fluorescence intensity per unit time (d the amount of increase in the fluorescence intensity/t), and the abscissa indicates the temperature (° C.).
Figure 6D:
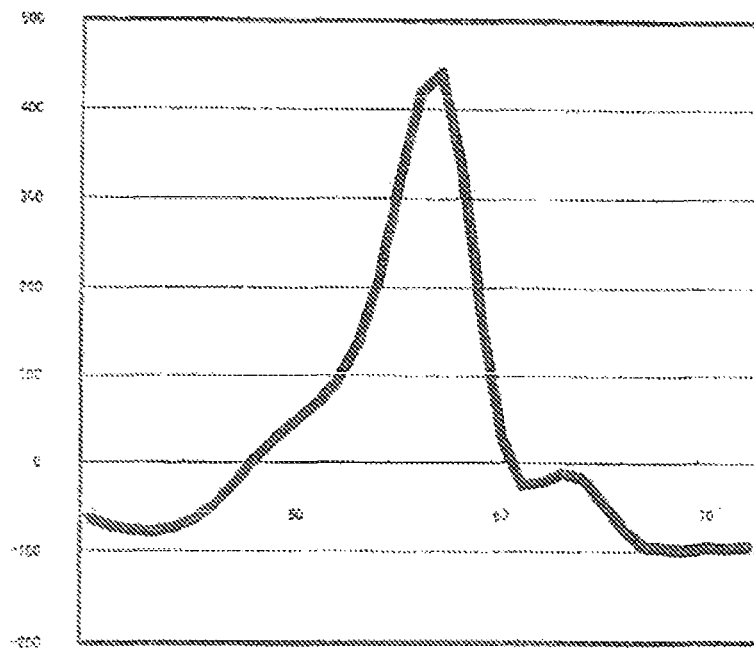
FIG. 6D shows change in the amount of change in the fluorescence intensity of TAMRA per unit time (d the amount of increase in the fluorescence intensity/t) in Tm analysis for the plasmid containing G895T (V299L) (5% mutation content) in Example 4-4 using the probe of SEQ ID NO:20. The ordinate indicates the amount of change in the fluorescence intensity per unit time (d the amount of increase in the fluorescence intensity/t), and the abscissa indicates the temperature (° C.).

On the other hand, referring to FIG. 3B, when the detection probe of Comparative Example 1 was used, the detection peak could be hardly observed, and the presence/absence of the mutation could not be known. From the above results, it could be understood that fluorescent labeling of any one of c in the probe is not necessarily effective, and that fluorescent labeling of c which is the complementary nucleotide of g at position 125 is important.

EXAMPLE 2

Point Mutation (T→C) at Nucleotide Position 757 in ab1 Gene

By using the probe of the present invention, PCR and Tm analysis were carried out for the point mutation (T→C) at nucleotide position 757 in the ab1 gene using a fully automatic SNPs testing device (trade name: i-densy (trademark), manufactured by ARKRAY, Inc.).

A plasmid in which the normal ab1 gene sequence (SEQ ID NO:3) having no mutation for T at nucleotide position 135 shown in SEQ ID NO:3 was inserted (wtDNA), and a plasmid in which the mutant ab1 gene (ab1 tyrosine kinase T757C (Y2531); SEQ ID NO:4) having the mutation from T to C at the nucleotide position 135 was inserted (mtDNA) were mixed together at a predetermined ratio (mtDNA: wtDNA=100 copies:900 copies) (10% mutation content), and the resulting mixture was diluted to 1000 copies/μL, to provide a template nucleic acid to be used for the reaction. The detection probe P2 was evaluated also for mutation contents of 20% and 0%. The reaction solution was formulated as shown in Table 3. The PCR reaction was carried out by treatment at 95° C. for 60 seconds, followed 50 cycles of 95° C. for 1 second and 58° C. for 30 seconds. Thereafter, treatment was carried out at 95° C. for 1 second and then at 40° C. for 60 seconds, followed by heating the reaction solution from 40° C. to 95° C. at a temperature increase rate of 1° C./3 seconds, while measuring change in the fluorescence intensity with time (WAVE3: 585-700 nm).

TABLE 3

| Reaction liquid volume: | 50 μl |
|---|---|
| 1 × PCR buffer | |
| dNTP | 0.2 mM |
| MgCl$_2$ | 1.5 mM |
| Taq polymerase (manufactured by ARKRAY, Inc.) | 1.88 U/test |
| Probe | 0.1 μM |
| Sense primer | 2 μM |
| Antisense primer | 1 μM |
| Template nucleic acid | 4 μl |

```
Sense primer
                                    SEQ ID NO: 23
5'-gacaagtgggagatggaacgc-3'

Antisense primer
                                    SEQ ID NO: 24
5'-cacggccaccgtcagg-3'
```

Example 2-1

```
Detection probe P2
                                    SEQ ID NO: 10
5'-(TAMRA)-cacctccccgtGctg-P-3'
```

Example 2-2

```
Detection probe P3
                                    SEQ ID NO: 11
5'-(TAMRA)-cctccccgtGctggc-P-3'
```

Example 2-3

```
Detection probe P4
                                    SEQ ID NO: 12
5'-gtacacctccccgtGc-(TAMRA)-3'
```

The results are shown in FIG. 4. FIG. 4 shows graphs showing the results of Tm analysis, in which change in the fluorescence intensity according to increase in the temperature is shown. In FIG. 4, (A) shows the result of Example 2-1; (B) shows the result of Example 2-2; and (C) shows the result of Example 2-3. In terms of (A), as a result of PCR and Tm analysis using the detection probe P2, only the peak for wtDNA was observed at about 52° C. when the mutation content was 0% (I), and the peak for mtDNA at about 58° C. was observed in addition to the peak for wtDNA when the mutation content was 10% (II) or 20% (III). The height of the peak for mtDNA increased as the mutation content increased. As a result of PCR and Tm analysis using the detection probe P3, the peak for wtDNA was observed at about 56° C., and the peak for mtDNA was observed at about 62° C. (B). As a result of PCR and Tm analysis using the detection probe P4, the peak for wtDNA was observed at about 57° C., and the peak for mtDNA was observed at about 63° C. (C).

From these results, it was revealed that use of the detection probe P2 to P4 enables enhancement of the detection sensitivity for mtDNA even in cases where mtDNA and wtDNA coexist.

It was understood that fluorescent labeling of c which is the complementary nucleotide of g at nucleotide position 146, 144 or 134 in SEQ ID NO:4 is important.

EXAMPLE 3

Point Mutation (A→T) at Nucleotide Position 764 in ab1 Gene

By using the probe of the present invention, PCR and Tm analysis were carried out for the point mutation (A→T) at nucleotide position 764 in the ab1 gene using a fully automatic SNPs testing device (trade name: i-densy (trademark), manufactured by ARKRAY, Inc.).

An oligonucleotide (SEQ ID NO:27) complementary to the ab1 gene sequence having no mutation for A at nucleotide position 142 shown in SEQ ID NO:3 (wtDNA) and an oligonucleotide (SEQ ID NO:28) complementary to the mutant ab1 gene (ab1 tyrosine kinase A764T(E255V)) having the mutation from A to T at the nucleotide position 142 (mtDNA) were synthesized. The both were then mixed together at a predetermined ratio (mtDNA:wtDNA=1 μM:9 μM) (10% mutation content). For hybridization of the probes and detection of the fluorescence intensity, the reaction liquid having the composition shown in Table 4 below was added to the reaction tube, and treated at 95° C. for 1 second and then at 40° C. for 60 seconds, followed by heating the reaction liquid from 40° C. to 95° C. at a temperature increase rate of 1° C./3 seconds, while measuring change in the fluorescence intensity with time (WAVE3: 585-700 nm).

TABLE 4

| Volume of reaction liquid for Tm analysis: 1 × GeneTaq Buffer | 50 μl |
|---|---|
| Probe | 0.05 μM |
| Complementary strand oligonucleotide | 0.5 μM |

| Complementary strand oligonucleotide | Sequence |
|---|---|
| SEQ ID NO: 27 (Wt) | ggcgggggccagtacggggAggtgtacgagggcgtgtgga |
| SEQ ID NO: 28 (Mt) | ggcgggggccagtacggggTggtgtacgagggcgtgtgga |

Example 3-1

Detection probe P5

SEQ ID NO: 13

5'-cctcgtacaccAcccc-(TAMRA)-3'

Example 3-2

Detection probe P6

SEQ ID NO: 14

5'-(TAMRA)-cctcgtacaccAcccc-P-3'

Example 3-4

Detection probe P3'

SEQ ID NO: 16

5'-(TAMRA)-ccAccccgtactggcc-P-3'

The results are shown in FIG. 5. FIG. 5 shows graphs showing the results of Tm analysis, in which change in the fluorescence intensity according to increase in the temperature is shown. In FIG. 5, (A) shows the result of Example 3-1; (B) shows the result of Example 3-2; (C) shows the result of Example 3-3; and (D) shows the result of Example 3-4. As a result of Tm analysis using the detection probe P5, the peak for wtDNA was observed at about 56° C., and the peak for mtDNA was observed at about 62° C. (A). As a result of Tm analysis using the detection probe P6, the peak for wtDNA was observed at about 55° C., and the peak for mtDNA was observed at about 62° C. (B). As a result of Tm analysis using the detection probe P7, the peak for wtDNA was observed at about 50° C., and the peak for mtDNA was observed at about 59° C. (C). As a result of Tm analysis using the detection probe P3', the peak for wtDNA was observed at about 58° C., and the peak for mtDNA was observed at about 63° C. (D).

From these results, it was revealed that use of the detection probe P3', or P5 to P7 enables enhancement of the detection sensitivity for mtDNA even in cases where mtDNA and wtDNA coexist.

It was understood that fluorescent labeling of c which is the complementary nucleotide of g at position 138, 153, 150 or 144 in SEQ ID NO:5 is important.

EXAMPLE 4

Point Mutation (G→C/T) at Nucleotide Position 895 in ab1 Gene

By using the probe of the present invention, PCR and Tm analysis were carried out for the point mutation (G→C/T) at nucleotide position 895 in the ab1 gene using a fully automatic SNPs testing device (trade name: i-densy (trademark), manufactured by ARKRAY, Inc.).

A plasmid in which the normal ab1 gene sequence (SEQ ID NO:6) having no mutation for G at nucleotide position 126 shown in SEQ ID NO:6 was inserted (wtDNA), and a plasmid in which the mutant ab1 gene (ab1 tyrosine kinase G895C/T (V299L); SEQ ID NO:7 or 8) having the mutation from G to C or T at the nucleotide position 126 was inserted (mtDNA) were mixed together at a predetermined ratio (mtDNA:wtDNA=50 copies:950 copies) (5% mutation content), and the resulting mixture was diluted to 1000 copies/μL, to provide a template nucleic acid to be used for the reaction. The reaction solution was formulated as shown in Table 5. The PCR reaction was carried out by treatment at 95° C. for 60 seconds, followed by 50 cycles of 95° C. for 1 second and 64° C. for 15

Detection probe P7

SEQ ID NO: 15

5'-(TAMRA)-cgtacaccAccccgta-P-3' seconds. Thereafter, treatment was further carried out at 95° C. for 1 second and then at 40° C. for 60 seconds, followed by heating the reaction solution from 40° C. to 95° C. at a temperature increase rate of 1° C./3 seconds, while measuring change in the fluorescence intensity with time (WAVE2: 520-555 nm, WAVE3: 585 to 700 nm).

TABLE 5

| Reaction liquid volume: | 50 μl |
| --- | --- |
| 1 × PCR buffer | |
| dNTP | 0.2 mM |
| MgCl$_2$ | 1.5 mM |
| Taq polymerase (manufactured by ARKRAY, Inc.) | 1.88 U/test |
| Probe | 0.1 μM |
| Sense primer | 1 μM |
| Antisense primer | 2 μM |
| Template nucleic acid | 4 μl |

```
Sense primer
                                  SEQ ID NO: 25
5'-gaaagaagctgcagtcatgaaagagat-3'

Antisense primer
                                  SEQ ID NO: 26
5'-cgcgagaccctctcttcagagc-3'
```

Example 4-1

```
Detection probe P8
                                  SEQ ID NO: 17
5'-cctgCtgcagctcc-(BODIPY FL)-3'
```

Example 4-2

```
Detection probe P9
                                  SEQ ID NO: 18
5'-accctaacctgCtgc-(BODIPY FL)-3'
```

Example 4-3

```
Detection probe P8
                                  SEQ ID NO: 19
5'-aacctgTtgcagctcc-(TAMRA)-3'
```

Example 4-4

```
Detection probe P9
                                  SEQ ID NO: 20
5'-tcaaacaccctaacctgTtgc-(TAMRA)-3'
```

The results are shown in FIG. 6. FIG. 6 shows graphs showing the results of Tm analysis, in which change in the fluorescence intensity according to increase in the temperature is shown. In FIG. 6, (A) shows the result of Example 4-1; (B) shows the result of Example 4-2; (C) shows the result of Example 4-3; and (D) shows the result of Example 4-4. As a result of PCR and Tm analysis using the detection probe P8, the peak for wtDNA was observed at about 47° C., and the peak for mtDNA was observed at about 61° C. (A). As a result of PCR and Tm analysis using the detection probe P9, the peak for wtDNA was observed at about 44° C., and the peak for mtDNA was observed at about 58° C. (B). As a result of PCR and Tm analysis using the detection probe P8, the pea for wtDNA was observed at about 52° C., and the peak for mtDNA was observed at about 61° C. (C). As a result of PCR and Tm analysis using the detection probe P9, the peak for wtDNA was observed at about 58° C., and the peak for mtDNA was observed at about 63° C. (D).

From these results, it was revealed that use of the detection probe P8 or P9 enables enhancement of the detection sensitivity for mtDNA even in cases where mtDNA and wtDNA coexist.

It was understood that fluorescent labeling of c at nucleotide position 135 or 129 in SEQ ID NO:7 or 8 is important.

Based on the results of Examples 1 to 4, use of the probes P1 to P9 (SEQ ID NOs:9 to 20) allowed observation of change in the fluorescence intensity which can be analyzed by Tm analysis, for the polymorphisms of the abl gene (T1076G (F359C), T757C(Y253H), A764T (E255V) and G895C/T (V299L)). That is, each variant has another peak in addition to the peak for the wild type, and shows a unique pattern of change in the amount of change in the fluorescence intensity. Therefore, by using the probes P1 to P9 (SEQ ID NOs:9 to 20), polymorphisms in the abl gene can be detected.

INDUSTRIAL APPLICABILITY

The present invention can be suitably used in the fields of medical treatment, diagnosis, research and the like.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A probe consisting of a fluorescent dye and an oligonucleotide, wherein the oligonucleotide consists of the oligonucleotide sequence of SEQ ID NO: 9, and the nucleotide base at the first position from the 3' end of the oligonucleotide is labeled with the fluorescent dye.

2. The probe according to claim 1, wherein said probe emits fluorescence when the probe is not hybridized with a target sequence, and the fluorescence intensity decreases or increases when the probe is hybridized with the target sequence.

3. The probe according to claim 2, wherein said probe emits fluorescence when the probe is not hybridized with a target sequence, and the fluorescence intensity decreases when the probe is hybridized with the target sequence.

4. The probe according to claim 1, wherein said probe is a probe for melting curve analysis.

5. A reagent kit for detecting a polymorphism in ab1 gene, said kit comprising the probe according to claim 1.

6. The reagent kit according to claim 5, further comprising primers for amplifying a region comprising a sequence in the nucleotide sequence of SEQ ID NO: 1 in the ab1 gene, with which the probe according to claim 1 hybridizes.

7. The probe according to claim 1, wherein the oligonucleotide is not labeled with a fluorescent dye at the 5'-end.

8. A method for detecting a polymorphism in ab1 gene, which method comprises using the probe according to claim 1.

9. A method for detecting a polymorphism in ab1 gene, said method comprising:
(I) bringing the probe according to claim 1 into contact with a sample containing DNA to allow said probe to hybridize with said DNA;
(II) changing the temperature to dissociate the hybrid-forming body between said DNA and said probe, and measuring fluctuation of a signal due to the dissociation of the hybrid-forming body;

(III) determining Tm value by analyzing said fluctuation of a signal; and
(IV) determining the presence/absence of the polymorphism of interest or abundance ratio of a nucleotide sequence(s) having the polymorphism, based on said Tm value.

10. The method according to claim 9, further comprising amplifying the DNA before said Step (I) or at the same time with said Step (I).

* * * * *

UNITED STATES PATENT AND TRADEMARK OFFICE
CERTIFICATE OF CORRECTION

PATENT NO.         : 9,085,803 B2                                    Page 1 of 1
APPLICATION NO.    : 13/180306
DATED              : July 21, 2015
INVENTOR(S)        : Toshiya Hosomi It is certified that error appears in the above-identified patent and that said Letters Patent is hereby corrected as shown below:

On the Title Page, Item (73) should appear as follows:

Assignee: ARKRAY, Inc., Kyoto (JP)

Signed and Sealed this
Twenty-ninth Day of December, 2015

Michelle K. Lee
*Director of the United States Patent and Trademark Office*

SEQUENCE LISTING

```
<160> NUMBER OF SEQ ID NOS: 28

<210> SEQ ID NO 1
<211> LENGTH: 300
<212> TYPE: DNA
<213> ORGANISM: Homo sapiens

<400> SEQUENCE: 1
ctgagttcat gacctacggg aacctcctgg actacctgag ggagtgcaac cggcaggagg        60
tgaacgccgt ggtgctgctg tacatggcca ctcagatctc gtcagccatg gagtacctgg       120
```
agaagaaaaa cttcatccac aggtagggc ctggccaggc agcctgcgcc atggagtcac    180
agggcgtgga gccgggcagc cttttacaaa aagccccagc ctaggaggtc tcagggcgca    240
gcttctaacc tcagtgctgg caacacattg gaccttggaa caaaggcaaa cactaggctc    300

<210> SEQ ID NO 2
<211> LENGTH: 300
<212> TYPE: DNA
<213> ORGANISM: Homo sapiens

<400> SEQUENCE: 2
ctgagttcat gacctacggg aacctcctgg actacctgag ggagtgcaac cggcaggagg     60
tgaacgccgt ggtgctgctg tacatggcca ctcagatctc gtcagccatg gagtacctgg    120
agaagaaaaa ctgcatccac aggtagggc ctggccaggc agcctgcgcc atggagtcac    180
agggcgtgga gccgggcagc cttttacaaa aagccccagc ctaggaggtc tcagggcgca    240
gcttctaacc tcagtgctgg caacacattg gaccttggaa caaaggcaaa cactaggctc    300

<210> SEQ ID NO 3
<211> LENGTH: 300
<212> TYPE: DNA
<213> ORGANISM: Homo sapiens

<400> SEQUENCE: 3
ggctcatcac cacgctccat tatccagccc caaagcgcaa caagcccact gtctatggtg     60
tgtcccccaa ctacgacaag tgggagatgg aacgcacgga catcaccatg aagcacaagc    120
tgggcggggg ccagtacggg gaggtgtacg agggcgtgtg gaagaaatac agcctgacgg    180
tggccgtgaa gaccttgaag gtaggctggg actgccgggg gtgcccaggg tacgtggggc    240
aaggcgtctg ctggcattag gcgatgcatc tgcctggaag tctacctcct gcctgctgtc    300

<210> SEQ ID NO 4
<211> LENGTH: 300
<212> TYPE: DNA
<213> ORGANISM: Homo sapiens

<400> SEQUENCE: 4
ggctcatcac cacgctccat tatccagccc caaagcgcaa caagcccact gtctatggtg     60
tgtcccccaa ctacgacaag tgggagatgg aacgcacgga catcaccatg aagcacaagc    120
tgggcggggg ccagcacggg gaggtgtacg agggcgtgtg gaagaaatac agcctgacgg    180
tggccgtgaa gaccttgaag gtaggctggg actgccgggg gtgcccaggg tacgtggggc    240
aaggcgtctg ctggcattag gcgatgcatc tgcctggaag tctacctcct gcctgctgtc    300

<210> SEQ ID NO 5
<211> LENGTH: 300
<212> TYPE: DNA
<213> ORGANISM: Homo sapiens

<400> SEQUENCE: 5
ggctcatcac cacgctccat tatccagccc caaagcgcaa caagcccact gtctatggtg     60
tgtcccccaa ctacgacaag tgggagatgg aacgcacgga catcaccatg aagcacaagc    120
tgggcggggg ccagtacggg gtggtgtacg agggcgtgtg gaagaaatac agcctgacgg    180
tggccgtgaa gaccttgaag gtaggctggg actgccgggg gtgcccaggg tacgtggggc    240
aaggcgtctg ctggcattag gcgatgcatc tgcctggaag tctacctcct gcctgctgtc    300

```
<210> SEQ ID NO 6
<211> LENGTH: 300
<212> TYPE: DNA
<213> ORGANISM: Homo sapiens

<400> SEQUENCE: 6
cactgaaaag cacttcctga ataatttca ccttcgtttt tttccttctg caggaggaca      60
ccatggaggt ggaagagttc ttgaaagaag ctgcagtcat gaaagagatc aaacaccta     120 acctggtgca gctccttggt gagtaagccc ggggctctga agagagggtc tcgcgccgca    180
cccccagggt gacacaggcg ctggggaaga cgcacgggcg gctcactgca caaaacctcg    240
ttggaatatt tgtgctctgc cgacgttcag ccgcgggtaa aatgaggcct gtatgggatg    300

<210> SEQ ID NO 7
<211> LENGTH: 300
<212> TYPE: DNA
<213> ORGANISM: Homo sapiens

<400> SEQUENCE: 7
cactgaaaag cacttcctga ataatttca ccttcgtttt tttccttctg caggaggaca      60
ccatggaggt ggaagagttc ttgaaagaag ctgcagtcat gaaagagatc aaacaccta     120 acctgctgca gctccttggt gagtaagccc ggggctctga agagagggtc tcgcgccgca    180
cccccagggt gacacaggcg ctggggaaga cgcacgggcg gctcactgca caaaacctcg    240
ttggaatatt tgtgctctgc cgacgttcag ccgcgggtaa aatgaggcct gtatgggatg    300

<210> SEQ ID NO 8
<211> LENGTH: 300
<212> TYPE: DNA
<213> ORGANISM: Homo sapiens

<400> SEQUENCE: 8
cactgaaaag cacttcctga ataatttca ccttcgtttt tttccttctg caggaggaca      60
ccatggaggt ggaagagttc ttgaaagaag ctgcagtcat gaaagagatc aaacaccta     120 acctgttgca gctccttggt gagtaagccc ggggctctga agagagggtc tcgcgccgca    180
cccccagggt gacacaggcg ctggggaaga cgcacgggcg gctcactgca caaaacctcg    240
ttggaatatt tgtgctctgc cgacgttcag ccgcgggtaa aatgaggcct gtatgggatg    300

<210> SEQ ID NO 9
<211> LENGTH: 19
<212> TYPE: DNA
<213> ORGANISM: Artificial Sequence
<220> FEATURE:
<223> OTHER INFORMATION: probe

<400> SEQUENCE: 9
cctgtggatg cagtttttc                                                  19

<210> SEQ ID NO 10
<211> LENGTH: 15
<212> TYPE: DNA
<213> ORGANISM: Artificial Sequence
<220> FEATURE:
<223> OTHER INFORMATION: probe

<400> SEQUENCE: 10
cacctccccg tgctg                                                      15

<210> SEQ ID NO 11
```

```
<211> LENGTH: 15
<212> TYPE: DNA
<213> ORGANISM: Artificial Sequence
<220> FEATURE:
<223> OTHER INFORMATION: probe

<400> SEQUENCE: 11
cctccccgtg ctggc                                                      15

<210> SEQ ID NO 12
<211> LENGTH: 16
<212> TYPE: DNA
<213> ORGANISM: Artificial Sequence
<220> FEATURE:
<223> OTHER INFORMATION: probe

<400> SEQUENCE: 12
gtacacctcc ccgtgc                                                     16

<210> SEQ ID NO 13
<211> LENGTH: 16
<212> TYPE: DNA
<213> ORGANISM: Artificial Sequence
<220> FEATURE:
<223> OTHER INFORMATION: probe

<400> SEQUENCE: 13
cctcgtacac cacccc                                                     16

<210> SEQ ID NO 14
<211> LENGTH: 16
<212> TYPE: DNA
<213> ORGANISM: Artificial Sequence
<220> FEATURE:
<223> OTHER INFORMATION: probe

<400> SEQUENCE: 14
cctcgtacac cacccc                                                     16

<210> SEQ ID NO 15
<211> LENGTH: 16
<212> TYPE: DNA
<213> ORGANISM: Artificial Sequence
<220> FEATURE:
<223> OTHER INFORMATION: probe

<400> SEQUENCE: 15
cgtacaccac cccgta                                                     16

<210> SEQ ID NO 16
<211> LENGTH: 16
<212> TYPE: DNA
<213> ORGANISM: Artificial Sequence
<220> FEATURE:
<223> OTHER INFORMATION: probe

<400> SEQUENCE: 16
ccaccccgta ctggcc                                                     16

<210> SEQ ID NO 17
<211> LENGTH: 14
<212> TYPE: DNA
<213> ORGANISM: Artificial Sequence
<220> FEATURE:
<223> OTHER INFORMATION: probe

<400> SEQUENCE: 17
```

```
cctgctgcag ctcc                                                      14

<210> SEQ ID NO 18
<211> LENGTH: 15
<212> TYPE: DNA
<213> ORGANISM: Artificial Sequence
<220> FEATURE:
<223> OTHER INFORMATION: probe

<400> SEQUENCE: 18
accctaacct gctgc                                                     15

<210> SEQ ID NO 19
<211> LENGTH: 16
<212> TYPE: DNA
<213> ORGANISM: Artificial Sequence
<220> FEATURE:
<223> OTHER INFORMATION: probe

<400> SEQUENCE: 19
aacctgttgc agctcc                                                    16

<210> SEQ ID NO 20
<211> LENGTH: 21
<212> TYPE: DNA
<213> ORGANISM: Artificial Sequence
<220> FEATURE:
<223> OTHER INFORMATION: probe

<400> SEQUENCE: 20
tcaaacaccc taacctgttg c                                              21

<210> SEQ ID NO 21
<211> LENGTH: 28
<212> TYPE: DNA
<213> ORGANISM: Artificial Sequence
<220> FEATURE:
<223> OTHER INFORMATION: primer

<400> SEQUENCE: 21
ggccggcccc gtggtgctgc tgtacatg                                       28

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
tccatggcgc aggctgcctg                                                20

<210> SEQ ID NO 23
<211> LENGTH: 21
<212> TYPE: DNA
<213> ORGANISM: Artificial Sequence
<220> FEATURE:
<223> OTHER INFORMATION: primer

<400> SEQUENCE: 23
gacaagtggg agatggaacg c                                              21

<210> SEQ ID NO 24
<211> LENGTH: 16
<212> TYPE: DNA
```

-continued

```
<213> ORGANISM: Artificial Sequence
<220> FEATURE:
<223> OTHER INFORMATION: primer

<400> SEQUENCE: 24
cacggccacc gtcagg                                                       16

<210> SEQ ID NO 25
<211> LENGTH: 27
<212> TYPE: DNA
<213> ORGANISM: Artificial Sequence
<220> FEATURE:
<223> OTHER INFORMATION: primer

<400> SEQUENCE: 25
gaaagaagct gcagtcatga aagagat                                           27

<210> SEQ ID NO 26
<211> LENGTH: 22
<212> TYPE: DNA
<213> ORGANISM: Artificial Sequence
<220> FEATURE:
<223> OTHER INFORMATION: primer

<400> SEQUENCE: 26
cgcgagaccc tctcttcaga gc                                                22

<210> SEQ ID NO 27
<211> LENGTH: 40
<212> TYPE: DNA
<213> ORGANISM: Artificial Sequence
<220> FEATURE:
<223> OTHER INFORMATION: oligonucleotide

<400> SEQUENCE: 27 ggcggggcc agtacgggga ggtgtacgag ggcgtgtgga                               40

<210> SEQ ID NO 28
<211> LENGTH: 40
<212> TYPE: DNA
<213> ORGANISM: Artificial Sequence
<220> FEATURE:
<223> OTHER INFORMATION: oligonucleotide

<400> SEQUENCE: 28 ggcggggcc agtacggggt ggtgtacgag ggcgtgtgga                               40
```